(12) United States Patent
Burns et al.

(10) Patent No.: US 10,745,424 B2
(45) Date of Patent: Aug. 18, 2020

(54) LADDERANE LIPID COMPOUNDS AND LIPOSOMES AND METHODS OF PREPARING AND USING THE SAME

(71) Applicant: The Board of Trustees of The Leland Stanford Junior University, Stanford, CA (US)

(72) Inventors: Noah Burns, Stanford, CA (US); Steven R. Shuken, Stanford, CA (US); Jaron A. M. Mercer, Stanford, CA (US); Carolyn M. Cohen, Stanford, CA (US)

(73) Assignee: THE BOARD OF TRUSTEES OF THE LELAND STANFORD JUNIOR UNIVERSITY, Stanford, CA (US)

( * ) Notice: Subject to any disclaimer, the term of this patent is extended or adjusted under 35 U.S.C. 154(b) by 0 days.

(21) Appl. No.: 16/327,735

(22) PCT Filed: Aug. 30, 2017

(86) PCT No.: PCT/US2017/049479
§ 371 (c)(1),
(2) Date: Feb. 22, 2019

(87) PCT Pub. No.: WO2018/045094
PCT Pub. Date: Mar. 8, 2018

(65) Prior Publication Data
US 2019/0177347 A1 Jun. 13, 2019

Related U.S. Application Data

(60) Provisional application No. 62/381,857, filed on Aug. 31, 2016.

(51) Int. Cl.
| | | |
|---|---|---|
| C07F 9/117 | (2006.01) |
| C07C 1/32 | (2006.01) |
| C07C 2/42 | (2006.01) |
| C07C 13/62 | (2006.01) |
| C07C 29/17 | (2006.01) |
| C07C 45/69 | (2006.01) |
| C07C 53/136 | (2006.01) |
| C07C 1/30 | (2006.01) |
| C07C 29/09 | (2006.01) |
| C07C 41/20 | (2006.01) |
| C07C 45/68 | (2006.01) |
| C07C 51/16 | (2006.01) |
| C07C 41/18 | (2006.01) |
| C07C 69/608 | (2006.01) |
| A61K 9/127 | (2006.01) |
| C07C 31/137 | (2006.01) |
| C07C 49/693 | (2006.01) |
| C07F 5/02 | (2006.01) |

(52) U.S. Cl.
CPC ............ *C07F 9/117* (2013.01); *A61K 9/1271* (2013.01); *C07C 1/30* (2013.01); *C07C 1/322* (2013.01); *C07C 2/42* (2013.01); *C07C 13/62* (2013.01); *C07C 29/09* (2013.01); *C07C 29/095* (2013.01); *C07C 29/172* (2013.01); *C07C 31/137* (2013.01); *C07C 41/18* (2013.01); *C07C 41/20* (2013.01); *C07C 45/68* (2013.01); *C07C 45/69* (2013.01); *C07C 49/693* (2013.01); *C07C 51/16* (2013.01); *C07C 53/136* (2013.01); *C07C 69/608* (2013.01); *C07F 5/025* (2013.01); *C07C 2602/18* (2017.05); *C07C 2603/40* (2017.05); *C07C 2603/52* (2017.05)

(58) Field of Classification Search
None
See application file for complete search history.

(56) References Cited

U.S. PATENT DOCUMENTS

| 7,524,966 B2 | 4/2009 | MacGillivray |
| 2011/0223207 A1 | 9/2011 | Mickle et al. |

FOREIGN PATENT DOCUMENTS

| WO | 2004035519 | 4/2004 |

OTHER PUBLICATIONS

Mascitti et al., J. of the American Chemical Society (2004), 126, pp. 15664-15665.*
Allen, T. & Cullis, P.; "Liposomal Drug Delivery Systems: From Concept to Clinical Applications"; Advanced Drug Delivery Reviews, 65 (2013) pp. 36-48.

(Continued)

*Primary Examiner* — Brian J Davis
(74) *Attorney, Agent, or Firm* — Kelly A. Tipson; Bret E. Field; Bozicevic, Field & Francis LLP

(57) ABSTRACT

Methods for preparing a variety of ladderane precursors, ladderane compounds and ladderane lipids are provided. Also provided are methods of preparing a liposome from the ladderane lipids disclosed herein, and compositions thereof. Aspects of the invention include encapsulated one or more cargo moieties in the liposome or compositions thereof and use of the subject liposome compositions as vehicles in drug delivery, imaging, diagnostics and other medical applications. Aspects of the methods disclosed herein include administering a liposomal composition comprising a pharmaceutical agent to a subject under conditions sufficient to deliver the composition to a site of interest in the subject, and release the pharmaceutical agent from the liposomal composition.

18 Claims, 7 Drawing Sheets

(56) References Cited

OTHER PUBLICATIONS

Boumann, et al.; "Biophysical properties of membrane lipids of anammox bacteria: I. Ladderane phospholipids form highly organized fluid membranes"; Biochimica et Biophysica Acta; (BBA)—Biomembranes; vol. 1788; Issue 7; 2009; pp. 1444-1451.

Burns, N.; "Selective Synthesis of Unusual Lipids"; E.J. Corey Award Symposium; ACS San Diego Meeting; Mar. 14, 2016.

Corey, E.J. & Mascitti, V.; "Total Synthesis of (+)-Pentacycloanammoxic Acid"; J. Am. Chem. Soc.; 2004; 126(48); pp. 15664-15665, (abstract).

Farivar, et al.; "Nano-drug Delivery of Apoptosis Activator 2 to AGS Cells by Liposomes Conjugated with Anti-TROP2 Antibody"; North American Journal of Medical Sciences; Nov. 2012; vol. 4; Issue 11; pp. 582-585.

Hopf, H., et al.; (2005), One-Pot Preparation of [n]Ladderanes by [2π+ 2π] Photocycloaddition. Eur. J. Org. Chem., 2005: 567-581. doi: 10.1002/ejoc.200400596, (abstract).

Li, W. & Fox, M.; "Syntheses, Characterization and Photophysics Studies of Photoactive Chromophore 2-Naphthyl-Labeled [n]-Ladderanes"; Journal of the American Chemical Society (1996); 118(47); 11752-11758, (abstract).

Mascitti, et al.; "Enantioselective Synthesis of Pentacycloanammoxic Acid"; J. Am. Chem. Soc.; 2006; 128; pp. 3118-3119.

Mercer, et al.; "Chemical Synthesis and Self-Assembly of a Ladderane Phospholipid"; J Am Chem Soc.; Dec. 14, 2016; 138(49): 15845-15848.

Sinninghe Damsté, et al.; "Linearly concatenated cyclobutane lipids form a dense bacterial membrane"; Nature vol. 419; http://www.nature.com/nature/journal/v419/n6908/full/nature01128.html; pp. 708-712 (Oct. 17, 2002), (abstract).

Hopf, et al. "Cubanes, Fenestranes, Ladderanes, Prismanes, Staffanes and Other Oligocyclobutanoids", PATAI'S Chemistry of Functional Groups, Cyclobutanes (2009), ChemInform, pp. 1-49.

National Center for Biotechnology Information, PubChem Database. SID 244852290, Source IBM, SID 244852290, https://pubchem.ncbi.nlm.nih.gov/substance/244852290 (accessed on Apr. 23, 2020), Data deposited in or computed by PubChem Mar. 17, 2015.

\* cited by examiner

| Entry | Lipid | Tails (sn-1, sn-2) | $T_m$ (°C) |
|---|---|---|---|
| 1 | [3][3]PC | [3], [3] | 15.18 ± 0.02 |
| 2 | [5][3]PC | [5], [3] | 11.8 ± 0.2 |
| 3 | [5][5]PC | [5], [5] | 68.2 ± 0.3 |
| 4 | DAPC | 20:0, 20:0 | 67.815 ± 0.002 |
| 5 | DSPC | 18:0, 18:0 | 57.08 ± 0.07 |
| 6 | DMPC | 14:0, 14:0 | 24.34 ± 0.01 |
| 7 | SOPC | 18:0, 18:1 | 4.119 ± 0.007 |
| 8 | DOPC | 18:1, 18:1 | −10.93 ± 0.03 |
| 9 | DEPC | 22:1, 22:1 | 15.85 ± 0.03 |

LADDERANE LIPID COMPOUNDS AND LIPOSOMES AND METHODS OF PREPARING AND USING THE SAME

CROSS-REFERENCE

This application claims the benefit of U.S. Provisional Patent Application No. 62/381,857, filed Aug. 31, 2016, which application is incorporated herein by reference in its entirety.

INTRODUCTION

Ladderane lipids, named for the ladder-like polycyclobutane motifs in their hydrophobic tails, are produced by anaerobic ammonium oxidizing (anammox) bacteria as a significant fraction of their membrane lipids. In a large intracellular compartment called the anammoxosome, anammox bacteria couple ammonium and nitrite to produce dinitrogen as their principle source of energy. Experimental and computational evidence suggests that ladderane lipids form a densely packed membrane around the anammoxosome and serve to limit the transmembrane diffusion of toxic and/or valuable metabolites from anammox catabolism. To date, biophysical characterization of Ladderane lipids is severely limited because individual ladderane species are unavailable for study. Slow growth of the producing organism and the inherent difficulty of purifying complex lipid mixtures have prohibited isolation of useful amounts of natural ladderane lipids.

Ladderane lipids, e.g., of phosphatidylcholine (PC), such as [5][3]PC (1), isolated from anammox enrichment cultures comprise a mixture containing [5]-ladderane tails, as in acid (2), and [3]-ladderane tails as in alcohol (3).

The nomenclature refers to the number of cyclobutane rings at the terminus of the chain. Only a handful of other natural products contain two fused cyclobutane rings, and only the ladderane lipids contain more than two. Pioneering synthetic efforts from Corey and Mascitti resulted in a racemic synthesis of [5]-ladderanoic acid (+/−)-2 and an entioselective synthesis of ent-2 (V. Mascitti, E. J. Corey, Total synthesis of (+/−)-pentacycloanammoxic acid. *J. Am. Chem. Soc.* 126, 15664-15665 (2004); V. Mascitti, E. J. Corey, Total synthesis of pentacycloanammoxic acid. *J. Am. Chem. Soc.* 128, 3118-3119 (2006)). No attempted synthesis of a [3]-ladderane compound (e.g. compound 3) or a ladderane lipid has been reported.

SUMMARY

Methods for preparing a variety of ladderane precursors, ladderane compounds and ladderane lipids are provided. The subject methods provide for the preparation of ladderane compounds in multi-gram quantities from commercially available materials. Also provided are methods of preparing a liposome from the ladderane lipids disclosed herein, and compositions thereof. Aspects of the invention include encapsulated cargo moieties in the liposome or compositions thereof and use of the subject liposomal compositions as vehicles in drug delivery, imaging, diagnostics and other medical applications. Aspects of the methods disclosed herein include administering a liposomal composition comprising a pharmaceutical agent to a subject under conditions sufficient to deliver the composition to a site of interest in the subject, and release the pharmaceutical agent from the liposomal composition. In some aspects, the methods are used for enhanced delivery of a cancer chemotherapy.

In contrast to conventional liposomal formulations that often leak drugs, ladderane lipid-based membranes are dense and comparatively more impermeable to small molecules, which makes them ideal vehicles to selectively penetrate cells for medical applications and in nanofabrication.

BRIEF DESCRIPTION OF THE FIGURES

The invention is best understood from the following detailed description when read in conjunction with the accompanying drawings. The patent or application file contains at least one drawing executed in color. It is emphasized that, according to common practice, the various features of the drawings are not to-scale. On the contrary, the dimensions of the various features are arbitrarily expanded or reduced for clarity. Included in the drawings are the following figures. It is understood that the drawings, described

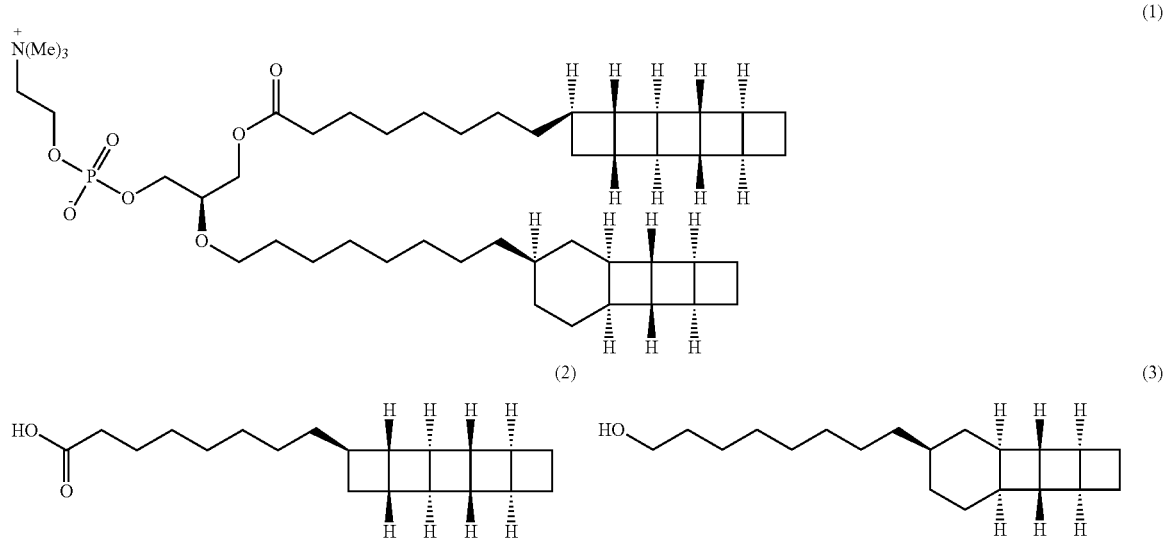

below, are for illustration purposes only. The drawings are not intended to limit the scope of the present teachings in any way.

Figure 1:
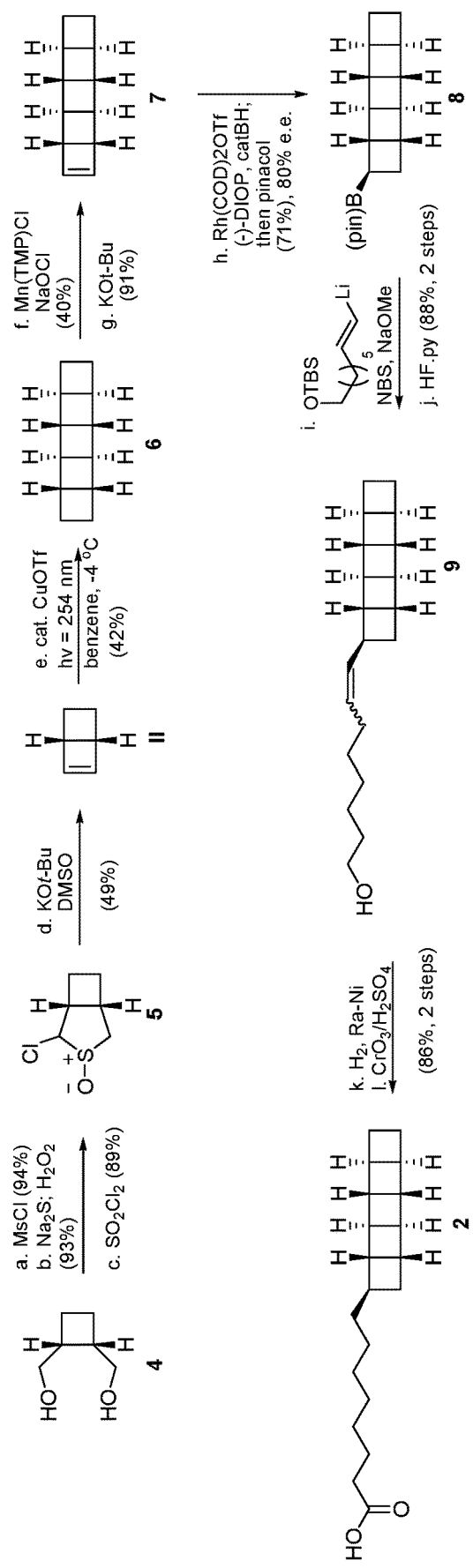

FIG. 1 depicts an exemplary reaction scheme for the preparation of [5]-ladderane compounds.

Figure 2:
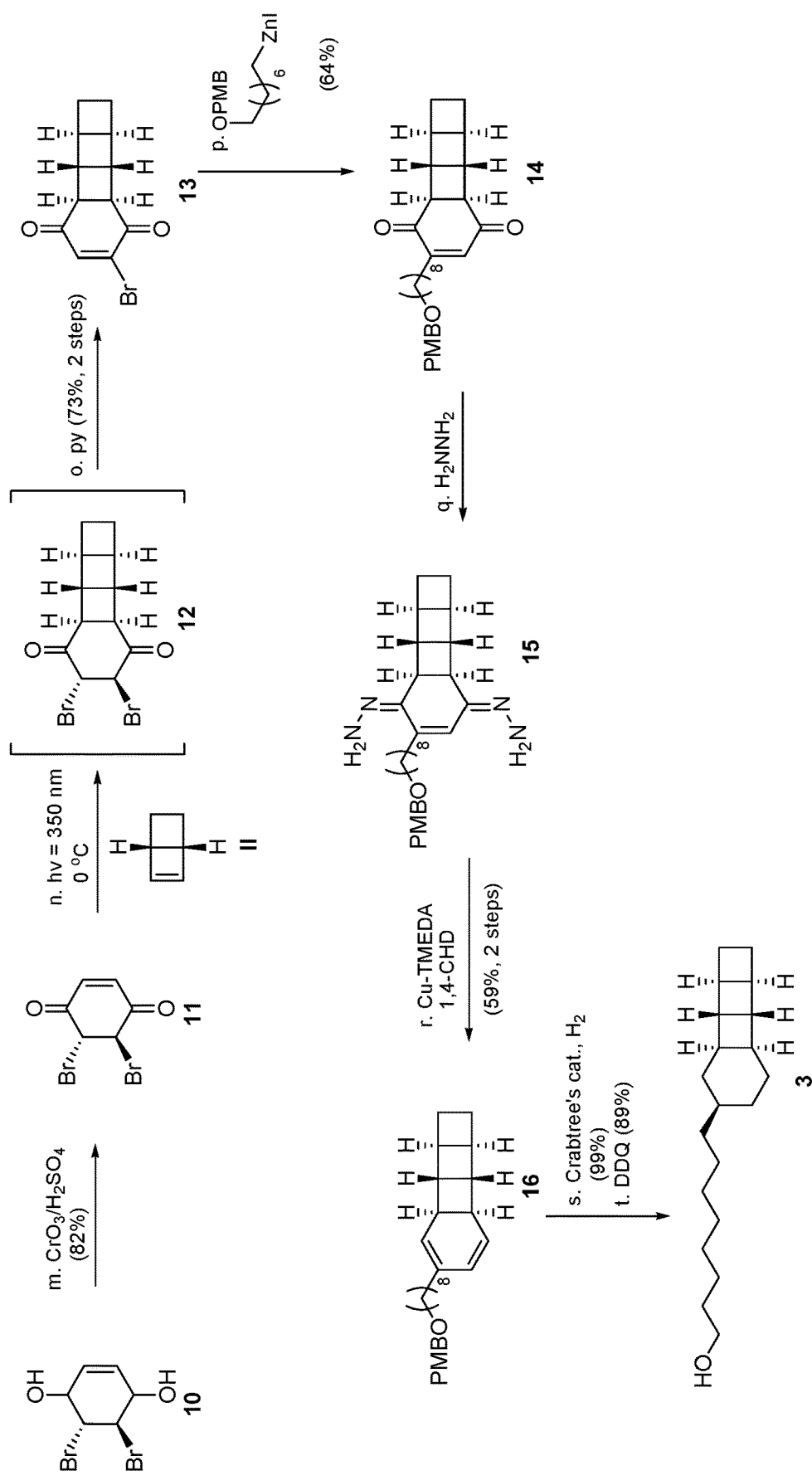

FIG. 2 depicts an exemplary reaction scheme for the preparation of [3]-ladderane compounds.

Figure 3:
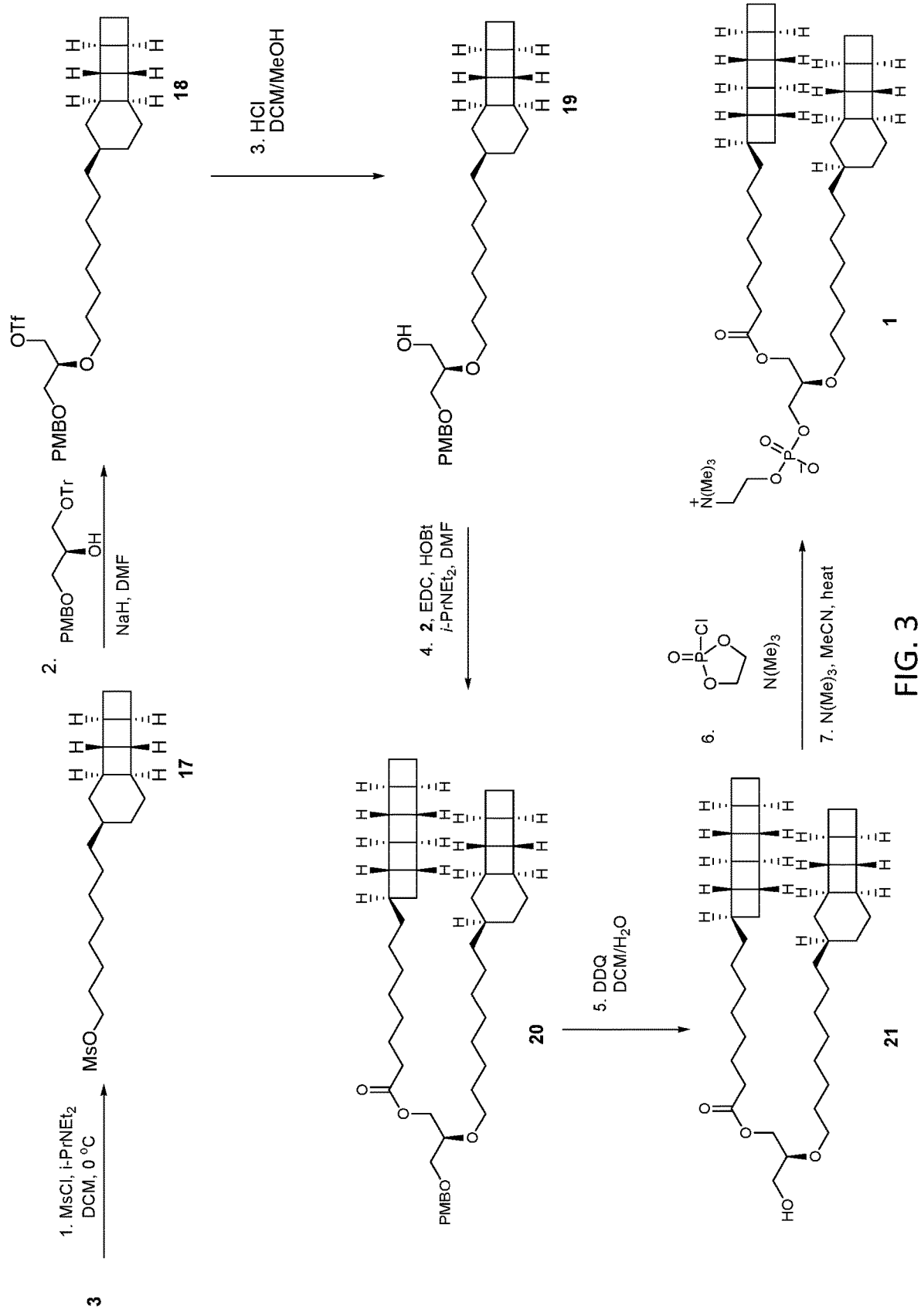

FIG. 3 depicts an exemplary reaction scheme for preparing ladderane lipid compounds from [5]-ladderane and [3]-ladderane compounds.

Figure 4:
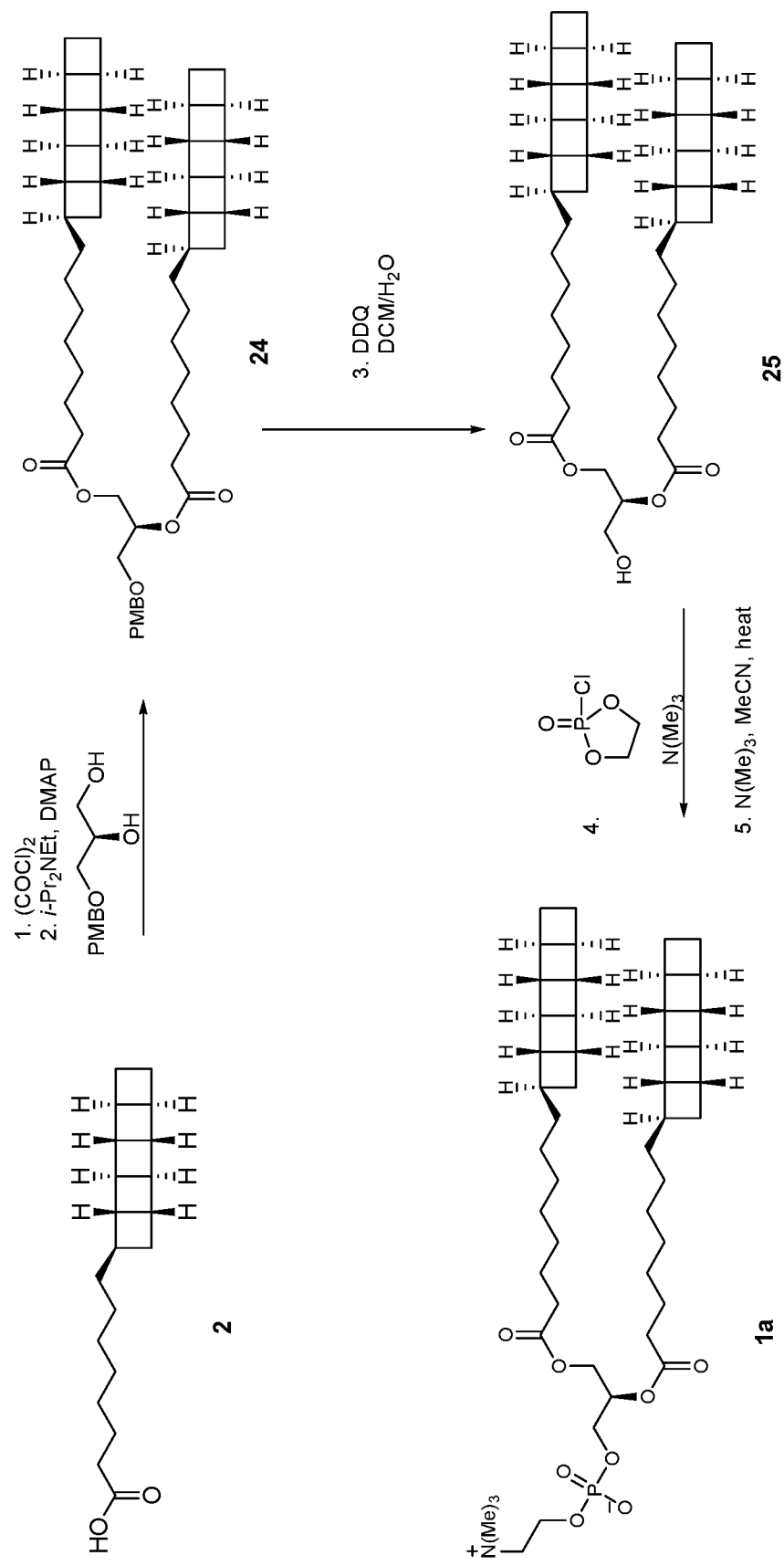

FIG. 4 illustrates an exemplary synthetic scheme for preparation of ladderane lipid compounds from [5]-ladderane compounds.

Figure 5:
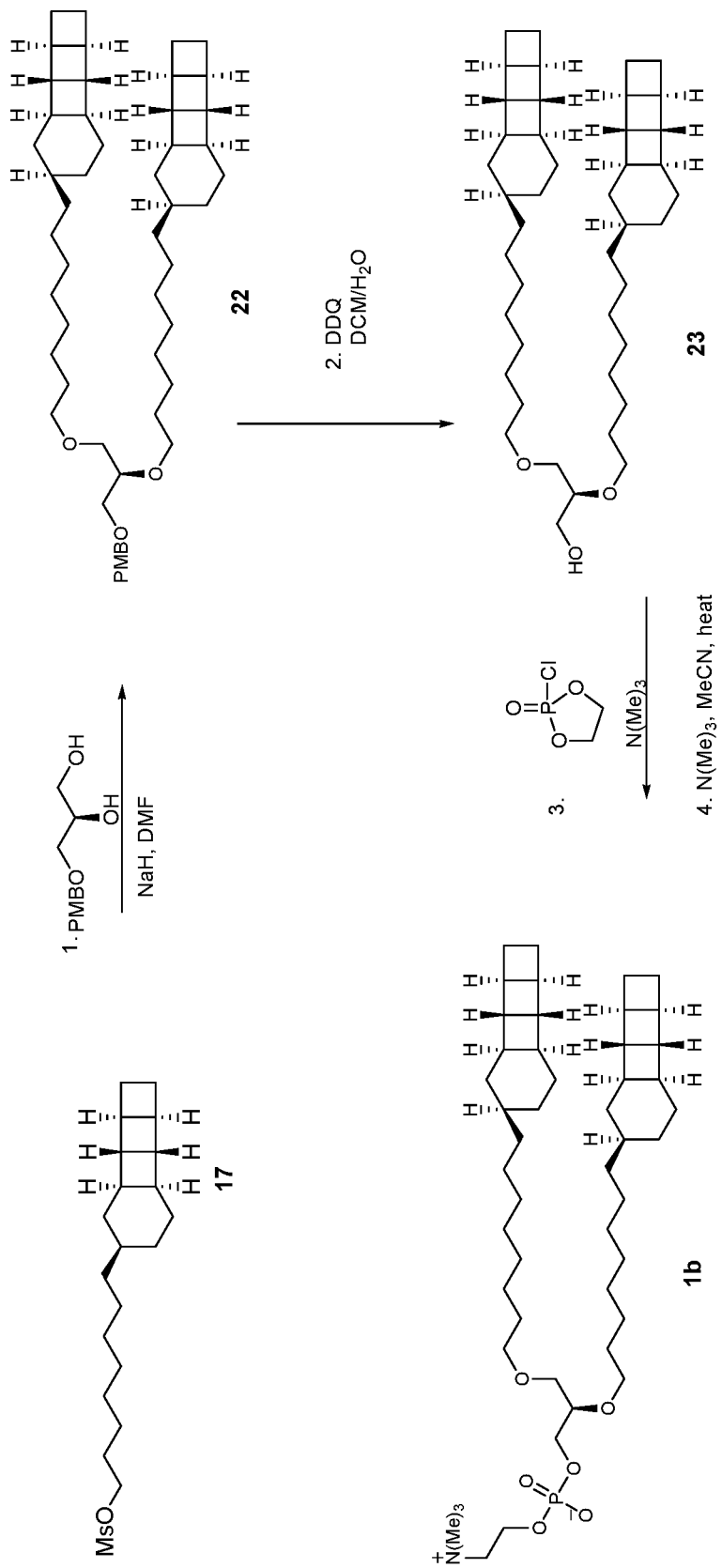

FIG. 5 illustrates an exemplary synthetic scheme for preparation of ladderane lipid compounds from [3]-ladderane compounds.

Figure 6:
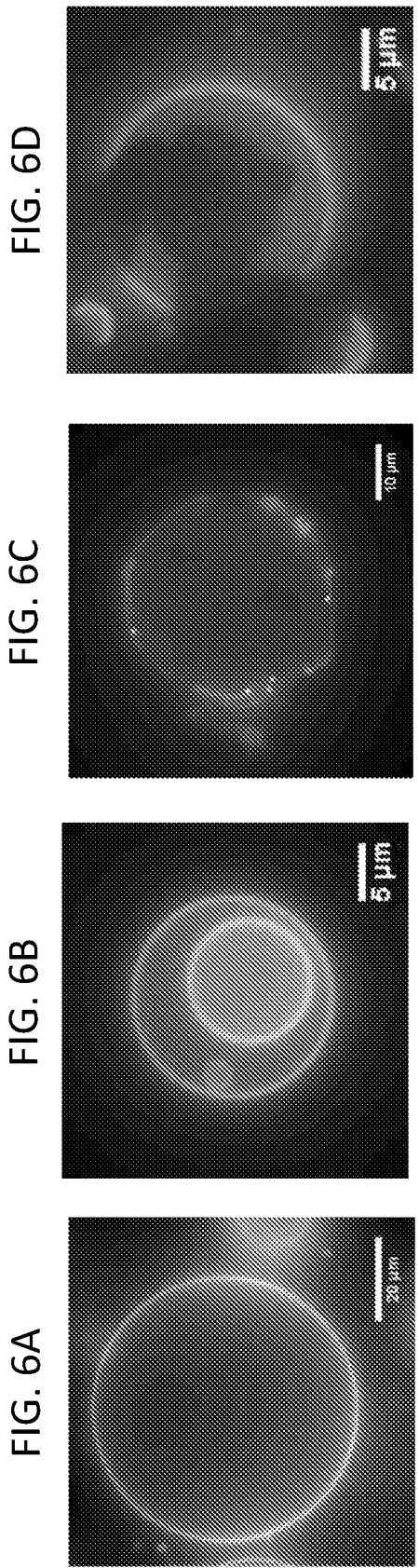

FIG. 6A illustrates fluorescence microscope image of giant unilamellar vesicles of [3][3]PC; FIG. 6B illustrates fluorescence microscope image of giant unilamellar vesicles of [5][3]PC; FIG. 6C illustrates fluorescence microscope image of giant unilamellar vesicles of [5][5]PC; and FIG. 6D illustrates fluorescence microscope image of giant unilamellar vesicles of a 1:1 mixture of [3][3]PC: [5][5]PC.

Figure 7:
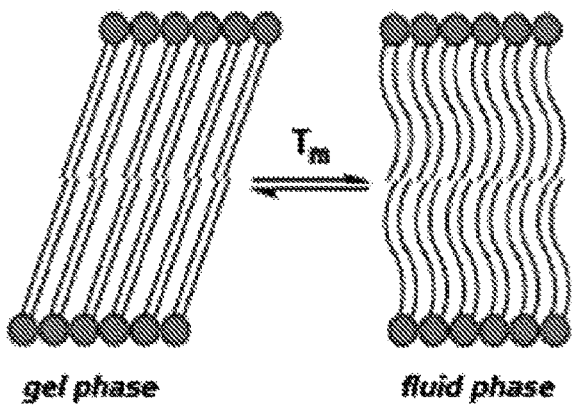

FIG. 7 illustrates melting temperatures ($T_m$) of aqueous dispersions of phosphatidylcholines (PCs) in 1:1 ethylene glycol:$NaH_2PO_4$ buffer measured by differential scanning calorimetry (DSC).

DEFINITIONS

Before describing exemplary embodiments in greater detail, the following definitions are set forth to illustrate and define the meaning and scope of the terms used in the description.

Unless defined otherwise, all technical and scientific terms used herein have the same meaning as commonly understood by one of ordinary skill in the art to which this invention belongs. Still, certain terms are defined below for the sake of clarity and ease of reference.

It must be noted that as used herein and in the appended claims, the singular forms "a", "an", and "the" include plural referents unless the context clearly dictates otherwise. For example, the term "a primer" refers to one or more primers, i.e., a single primer and multiple primers. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

Numeric ranges are inclusive of the numbers defining the range.

The methods described herein include multiple steps. Each step may be performed after a predetermined amount of time has elapsed between steps, as desired. As such, the time between performing each step may be 1 second or more, 10 seconds or more, 30 seconds or more, 60 seconds or more, 5 minutes or more, 10 minutes or more, 60 minutes or more and including 5 hours or more. In certain embodiments, each subsequent step is performed immediately after completion of the previous step. In other embodiments, a step may be performed after an incubation or waiting time after completion of the previous step, e.g., a few minutes to an overnight waiting time. In certain cases, a step may be performed using materials (e.g., intermediate materials that have been previously prepared using any convenient methods) that have been stored for any convenient period of time.

"Alkyl" refers to monovalent saturated aliphatic hydrocarbyl groups having from 1 to 20 carbon atoms and such as 1 to 10 carbon atoms, or 1 to 6, or 1 to 5, or 1 to 4, or 1 to 3 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—).

The term "substituted alkyl" refers to an alkyl group as defined herein wherein one or more carbon atoms in the alkyl chain have been optionally replaced with a heteroatom such as —O—, —N—, —S—, —S(O)$_n$— (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —$SO_2$-alkyl, —$SO_2$-aryl, —$SO_2$-heteroaryl, and —NR$^a$R$^b$, wherein R' and R" may be the same or different and are chosen from hydrogen, optionally substituted alkyl, cycloalkyl, alkenyl, cycloalkenyl, alkynyl, aryl, heteroaryl and heterocyclic.

"Alkylene" refers to divalent aliphatic hydrocarbyl groups having from 1 to 20 and in some cases, 1 to 10, or 1 to 6, or 1 to 3 carbon atoms that are either straight-chained or branched, and which are optionally interrupted with one or more groups selected from —O—, —NR$^{10}$—, —NR$^{10}$C(O)—, —C(O)NR$^{10}$— and the like. This term includes, by way of example, methylene (—$CH_2$—), ethylene (—$CH_2CH_2$—), n-propylene (—$CH_2CH_2CH_2$—), iso-propylene (—$CH_2CH(CH_3)$—), (—$C(CH_3)_2CH_2CH_2$—), (—$C(CH_3)_2CH_2C(O)$—), (—$C(CH_3)_2CH_2C(O)NH$—), (—$CH(CH_3)CH_2$—), and the like.

"Substituted alkylene" refers to an alkylene group having from 1 to 3 hydrogens replaced with substituents as described for carbons in the definition of "substituted" below.

The term "alkane" refers to alkyl group and alkylene group, as defined herein.

The term "alkylaminoalkyl", "alkylaminoalkenyl" and "alkylaminoalkynyl" refers to the groups R'NHR"— where R' is alkyl group as defined herein and R" is alkylene, alkenylene or alkynylene group as defined herein.

The term "alkaryl" or "aralkyl" refers to the groups -alkylene-aryl and -substituted alkylene-aryl where alkylene, substituted alkylene and aryl are defined herein.

"Alkoxy" refers to the group —O-alkyl, wherein alkyl is as defined herein. Alkoxy includes, by way of example, methoxy, ethoxy, n-propoxy, isopropoxy, n-butoxy, t-butoxy, sec-butoxy, n-pentoxy, and the like. The term "alkoxy" also refers to the groups alkenyl-O—, cycloalkyl-O—, cycloalkenyl-O—, and alkynyl-O—, where alkenyl, cycloalkyl, cycloalkenyl, and alkynyl are as defined herein.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "alkoxyamino" refers to the group —NH-alkoxy, wherein alkoxy is defined herein.

The term "haloalkoxy" refers to the groups alkyl-O— wherein one or more hydrogen atoms on the alkyl group have been substituted with a halo group and include, by way of examples, groups such as trifluoromethoxy, and the like.

The term "haloalkyl" refers to a substituted alkyl group as described above, wherein one or more hydrogen atoms on the alkyl group have been substituted with a halo group. Examples of such groups include, without limitation, fluoroalkyl groups, such as trifluoromethyl, difluoromethyl, trifluoroethyl and the like.

The term "alkylalkoxy" refers to the groups -alkylene-O-alkyl, alkylene-O-substituted alkyl, substituted alkylene-O-alkyl, and substituted alkylene-O-substituted alkyl wherein alkyl, substituted alkyl, alkylene and substituted alkylene are as defined herein.

The term "alkylthioalkoxy" refers to the group -alkylene-S-alkyl, alkylene-S-substituted alkyl, substituted alkylene-S-alkyl and substituted alkylene-S-substituted alkyl wherein alkyl, substituted alkyl, alkylene and substituted alkylene are as defined herein.

"Alkenyl" refers to straight chain or branched hydrocarbyl groups having from 2 to 20 carbon atoms and in some cases 2 to 10 carbon atoms, such as 2 to 7 carbon atoms, and having at least 1 and in some cases from 1 to 2 sites of double bond unsaturation. This term includes, by way of example, bi-vinyl, allyl, and but-3-en-1-yl. Included within this term are the cis and trans isomers or mixtures of these isomers.

The term "substituted alkenyl" refers to an alkenyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Allenyl" refers to straight chain or branched hydrocarbyl groups having from 2 to 20 carbon atoms and in some cases 2 to 10 carbon atoms, such as 2 to 7 carbon atoms and having a carbon atom having double bond unsaturation to each of its two adjacent carbon atoms. Included within this term are the stereo isomers or mixtures of these isomers.

The term "substituted allenyl" refers to an alkenyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Alkynyl" refers to straight or branched monovalent hydrocarbyl groups having from 2 to 20 carbon atoms and in some cases 2 to 10 carbon atoms, such as 2 to 7 carbon atoms, and having at least 1 and in some cases from 1 to 2 sites of triple bond unsaturation. Examples of such alkynyl groups include acetylenyl (—C≡CH), and propargyl (—CH$_2$C≡CH).

The term "substituted alkynyl" refers to an alkynyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, and —SO$_2$-heteroaryl.

"Alkynyloxy" refers to the group —O-alkynyl, wherein alkynyl is as defined herein. Alkynyloxy includes, by way of example, ethynyloxy, propynyloxy, and the like.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclyl-C(O)—, and substituted heterocyclyl-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. For example, acyl includes the "acetyl" group CH$_3$C(O)— "Acylamino" refers to the groups —NR$^{20}$C(O)alkyl, —NR$^{20}$C(O)substituted alkyl, N R$^{20}$C(O)cycloalkyl, —NR$^{20}$C(O)substituted cycloalkyl, —NR$^{20}$C(O)cycloalkenyl, —NR$^{20}$C(O)substituted cycloalkenyl, —NR$^{20}$C(O)alkenyl, —NR$^{20}$C(O)substituted alkenyl, —NR$^{20}$C(O)alkynyl, —NR$^{20}$C(O)substituted alkynyl, —NR$^{20}$C(O)aryl, —NR$^{20}$C(O)substituted aryl, —NR$^{20}$C(O)heteroaryl, —NR$^{20}$C(O)substituted heteroaryl, —NR$^{20}$C(O)heterocyclic, and —NR$^{20}$C(O)substituted heterocyclic, wherein R$^{20}$ is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonyl" or the term "aminoacyl" refers to the group —C(O)NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonylamino" refers to the group —NR$^{21}$(O)NR$^{22}$R$^{23}$ where R$^{21}$, R$^{22}$, and R$^{23}$ are independently selected from hydrogen, alkyl, aryl or cycloalkyl, or where two R groups are joined to form a heterocyclyl group.

The term "alkoxycarbonylamino" refers to the group —NRC(O)OR where each R is independently hydrogen, alkyl, substituted alkyl, aryl, heteroaryl, or heterocyclyl wherein alkyl, substituted alkyl, aryl, heteroaryl, and heterocyclyl are as defined herein.

The term "acyloxy" refers to the groups alkyl-C(O)O—, substituted alkyl-C(O)O—, cycloalkyl-C(O)O—, substituted cycloalkyl-C(O)O—, aryl-C(O)O—, heteroaryl-C(O)O—, and heterocyclyl-C(O)O— wherein alkyl, substituted alkyl, cycloalkyl, substituted cycloalkyl, aryl, heteroaryl, and heterocyclyl are as defined herein.

"Aminosulfonyl" refers to the group —SO$_2$NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic and where R$^{21}$ and R$^{22}$ are optionally joined together with the nitrogen bound thereto to form a heterocyclic or substituted heterocyclic group and alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Sulfonylamino" refers to the group —NR$^{21}$SO$_2$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the atoms bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aryl" or "Ar" refers to a monovalent aromatic carbocyclic group of from 6 to 18 carbon atoms having a single ring (such as is present in a phenyl group) or a ring system having multiple condensed rings (examples of such aromatic ring systems include naphthyl, anthryl and indanyl) which condensed rings may or may not be aromatic, provided that the point of attachment is through an atom of an aromatic ring. This term includes, by way of example, phenyl and naphthyl. Unless otherwise constrained by the definition for the aryl substituent, such aryl groups can optionally be substituted with from 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl.

"Aryloxy" refers to the group —O-aryl, wherein aryl is as defined herein, including, by way of example, phenoxy, naphthoxy, and the like, including optionally substituted aryl groups as also defined herein.

"Amino" refers to the group —NH$_2$.

The term "substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl, and heterocyclyl provided that at least one R is not hydrogen.

The term "azido" refers to the group —N$_3$.

"Carboxyl," "carboxy" or "carboxylate" refers to —CO$_2$H or salts thereof.

"Carboxyl ester" or "carboxy ester" or the terms "carboxyalkyl" or "carboxylalkyl" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)oxy" or "carbonate" refers to the groups —O—C(O)O-alkyl, —O—C(O)O-substituted alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-cycloalkenyl, —O—C(O)O-substituted cycloalkenyl, —O—C(O)O-heteroaryl, —O—C(O)O-substituted heteroaryl, —O—C(O)O-heterocyclic, and —O—C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" or "nitrile" refers to the group —CN.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, cyclooctyl and the like. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents, or from 1 to 3 substituents, selected from alkyl, substituted alkyl, alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Cycloalkenyl" refers to non-aromatic cyclic alkyl groups of from 3 to 10 carbon atoms having single or multiple rings and having at least one double bond and in some cases from 1 to 2 double bonds.

The term "substituted cycloalkenyl" refers to cycloalkenyl groups having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Cycloalkynyl" refers to non-aromatic cycloalkyl groups of from 5 to 10 carbon atoms having single or multiple rings and having at least one triple bond.

"Cycloalkoxy" refers to —O-cycloalkyl.

"Cycloalkenyloxy" refers to —O-cycloalkenyl.

"Halo" or "halogen" refers to fluoro, chloro, bromo, and iodo.

"Hydroxy" or "hydroxyl" refers to the group —OH.

"Heteroaryl" refers to an aromatic group of from 1 to 15 carbon atoms, such as from 1 to 10 carbon atoms and 1 to 10 heteroatoms selected from the group consisting of oxygen, nitrogen, and sulfur within the ring. Such heteroaryl groups can have a single ring (such as, pyridinyl, imidazolyl or furyl) or multiple condensed rings in a ring system (for example as in groups such as, indolizinyl, quinolinyl, benzofuran, benzimidazolyl or benzothienyl), wherein at least one ring within the ring system is aromatic and at least one ring within the ring system is aromatic, provided that the point of attachment is through an atom of an aromatic ring. In certain embodiments, the nitrogen and/or sulfur ring atom(s) of the heteroaryl group are optionally oxidized to provide for the N-oxide (N→O), sulfinyl, or sulfonyl moieties. This term includes, by way of example, pyridinyl, pyrrolyl, indolyl, thiophenyl, and furanyl. Unless otherwise constrained by the definition for the heteroaryl substituent, such heteroaryl groups can be optionally substituted with 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl, and trihalomethyl.

The term "heteroaralkyl" refers to the groups -alkylene-heteroaryl where alkylene and heteroaryl are defined herein. This term includes, by way of example, pyridylmethyl, pyridylethyl, indolylmethyl, and the like.

"Heteroaryloxy" refers to —O-heteroaryl.

"Heterocycle," "heterocyclic," "heterocycloalkyl," and "heterocyclyl" refer to a saturated or unsaturated group having a single ring or multiple condensed rings, including fused bridged and spiro ring systems, and having from 3 to 20 ring atoms, including 1 to 10 hetero atoms. These ring atoms are selected from the group consisting of nitrogen, sulfur, or oxygen, wherein, in fused ring systems, one or more of the rings can be cycloalkyl, aryl, or heteroaryl, provided that the point of attachment is through the non-aromatic ring. In certain embodiments, the nitrogen and/or sulfur atom(s) of the heterocyclic group are optionally oxidized to provide for the N-oxide, —S(O)—, or —SO$_2$— moieties.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

Unless otherwise constrained by the definition for the heterocyclic substituent, such heterocyclic groups can be optionally substituted with 1 to 5, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and fused heterocycle.

"Heterocyclyloxy" refers to the group —O-heterocyclyl.

The term "heterocyclylthio" refers to the group heterocyclic-S—.

The term "heterocyclene" refers to the diradical group formed from a heterocycle, as defined herein.

The term "hydroxyamino" refers to the group —NHOH.

"Nitro" refers to the group —NO$_2$.

"Oxo" refers to the atom (=O).

"Sulfonyl" refers to the group SO$_2$-alkyl, SO$_2$-substituted alkyl, SO$_2$-alkenyl, SO$_2$-substituted alkenyl, SO$_2$-cycloalkyl, SO$_2$-substituted cylcoalkyl, SO$_2$-cycloalkenyl, SO$_2$-substituted cylcoalkenyl, SO$_2$-aryl, SO$_2$-substituted aryl, SO$_2$-heteroaryl, SO$_2$-substituted heteroaryl, SO$_2$-heterocyclic, and SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Sulfonyl includes, by way of example, methyl-SO$_2$—, phenyl-SO$_2$—, and 4-methylphenyl-SO$_2$—.

"Sulfonyloxy" refers to the group —OSO$_2$-alkyl, OSO$_2$-substituted alkyl, OSO$_2$-alkenyl, OSO$_2$-substituted alkenyl, OSO$_2$-cycloalkyl, OSO$_2$-substituted cylcoalkyl, OSO$_2$-cycloalkenyl, OSO$_2$-substituted cylcoalkenyl, OSO$_2$-aryl, OSO$_2$-substituted aryl, OSO$_2$-heteroaryl, OSO$_2$-substituted heteroaryl, OSO$_2$-heterocyclic, and OSO$_2$ substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

The term "aminocarbonyloxy" refers to the group —OC(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

"Thiol" refers to the group —SH.

"Thioxo" or the term "thioketo" refers to the atom (=S).

"Alkylthio" or the term "thioalkoxy" refers to the group —S-alkyl, wherein alkyl is as defined herein. In certain embodiments, sulfur may be oxidized to —S(O)—. The sulfoxide may exist as one or more stereoisomers.

The term "substituted thioalkoxy" refers to the group —S-substituted alkyl.

The term "thioaryloxy" refers to the group aryl-S— wherein the aryl group is as defined herein including optionally substituted aryl groups also defined herein.

The term "thioheteroaryloxy" refers to the group heteroaryl-S— wherein the heteroaryl group is as defined herein including optionally substituted aryl groups as also defined herein.

The term "thioheterocyclooxy" refers to the group heterocyclyl-S— wherein the heterocyclyl group is as defined herein including optionally substituted heterocyclyl groups as also defined herein.

In addition to the disclosure herein, the term "substituted," when used to modify a specified group or radical, can also mean that one or more hydrogen atoms of the specified group or radical are each, independently of one another, replaced with the same or different substituent groups as defined below.

In addition to the groups disclosed with respect to the individual terms herein, substituent groups for substituting for one or more hydrogens (any two hydrogens on a single carbon can be replaced with =O, =NR$^{70}$, =N—OR$^{70}$, =N$_2$ or =S) on saturated carbon atoms in the specified group or radical are, unless otherwise specified, —R$^{60}$, halo, =O, —OR$^{70}$, —SR$^{70}$, —NR$^{80}$R$^{80}$, trihalomethyl, —CN, —OCN, —SCN, —NO, —NO$_2$, =N$_2$, —N$_3$, —SO$_2$R$^{70}$, —SO$_2$O$^-$M$^+$, —SO$_2$OR$^{70}$, —OSO$_2$O$^-$M$^+$, —OSO$_2$O$^-$M$^+$, —OSO$_2$OR$^{70}$, —P(O)(O$^-$)$_2$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —C(O)O$^-$M$^+$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O)O$^-$M$^+$, —OC(O)OR$^{70}$, —OC(S)OR$^{70}$, —NR$^{70}$C(O)R$^{70}$, —NR$^{70}$C(S)R$^{70}$, —NR$^{70}$CO$_2$$^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$ is selected from the group consisting of optionally substituted alkyl, cycloalkyl, heteroalkyl, heterocycloalkylalkyl, cycloalkylalkyl, aryl, arylalkyl, heteroaryl and heteroarylalkyl, each R$^{70}$ is independently hydrogen or R$^{60}$; each R$^{80}$ is independently R$^{70}$ or alternatively, two R$^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or C$_1$-C$_3$ alkyl substitution; and each M$^+$ is a counter ion with a positive charge. Each M$^+$ may independently be, for example, an alkali ion, such as K$^+$, Na$^+$, Li$^+$; an ammonium ion, such as $^+$N(R$^{60}$)$_4$; or an alkaline earth ion, such as [Ca$^{2+}$]$_{0.5}$, [Mg$^{2+}$]$_{0.5}$, or [Ba$^{2+}$]$_{0.5}$ ("subscript 0.5 means that one of the counter ions for such divalent alkali earth ions can be an ionized form of a compound of the invention and the other a typical counter ion such as chloride, or two ionized compounds disclosed herein can serve as counter ions for such divalent alkali earth ions, or a doubly ionized compound of the invention can serve as the counter ion for such divalent alkali earth ions). As specific examples, —NR$^{80}$R$^{80}$ is meant to include —NH$_2$, —NH-alkyl, N-pyrrolidinyl, N-piperazinyl, 4N-methyl-piperazin-1-yl and N-morpholinyl.

In addition to the disclosure herein, substituent groups for hydrogens on unsaturated carbon atoms in "substituted" alkene, alkyne, aryl and heteroaryl groups are, unless otherwise specified, —R$^{60}$, halo, —O$^-$M$^+$, —OR$^{70}$, —SR$^{70}$, —S$^-$M$^+$, —NR$^{80}$R$^{80}$, trihalomethyl, —CF$_3$, —CN, —OCN, —SCN, —NO, —NO$_2$, —N$_3$, —SO$_2$R$^{70}$, —SO$_3$$^-$M$^+$, —SO$_3$R$^{70}$, —OSO$_2$R$^{70}$, —OSO$_3$$^-$M$^+$, —OSO$_3$R$^{70}$, —PO$_3$$^{-2}$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —CO$_2$$^-$M$^+$, —CO$_2$R$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OCO$_2$$^-$M$^+$, —OCO$_2$R$^{70}$, —OC(S)OR$^{70}$, —NR$^{70}$C(O)R$^{70}$, —NR$^{70}$C(S)R$^{70}$, —NR$^{70}$CO$_2$$^-$M$^+$, —NR$^{70}$CO$_2$R$^{70}$, —NR$^{70}$C(S)OR$^{70}$, —NR$^{70}$C(O)NR$^{80}$R$^{80}$, —NR—NR$^{70}$C(NR$^{70}$)R$^{70}$ and —NR$^{70}$C(NR$^{70}$)NR$^{80}$, where R$^{60}$, R$^{70}$, R$^{80}$ and M$^+$ are as previously defined, provided that in case of substituted alkene or alkyne, the substituents are not —O$^-$M$^+$, —OR$^{70}$, —SR$^{70}$, or —S$^-$M$^+$.

In addition to the groups disclosed with respect to the individual terms herein, substituent groups for hydrogens on nitrogen atoms in "substituted" heteroalkyl and cycloheteroalkyl groups are, unless otherwise specified, —R$^{60}$, —O$^-$M$^+$, —OR$^{70}$, SR$^{70}$, —S$^-$NM$^+$, —NR$^{80}$R$^{80}$, trihalomethyl, —CF$_3$, —CN, —NO, —NO$_2$, —S(O)$_2$R$^{70}$, —S(O)$_2$O$^-$M$^-$, —S(O)$_2$OR$^{70}$, —OS(O)$_2$R$^{70}$, —OS(O)$_2$O$^-$M$^+$, —OS(O)$_2$OR$^{70}$, —P(O)(O$^-$)$_2$(M$^-$)$_2$, —P(O)(OR$^{70}$)O$^-$M$^+$, —P(O)(OR$^{70}$)(OR$^{70}$), —C(O)R$^{70}$, —C(S)R$^{70}$, —C(NR$^{70}$)R$^{70}$, —C(O)OR$^{70}$, —C(S)OR$^{70}$, —C(O)$_{NR}$$^{80}$R$^{80}$, —C(NR$^{70}$)NR$^{80}$R$^{80}$, —OC(O)R$^{70}$, —OC(S)R$^{70}$, —OC(O)OR$^{70}$, —OC(S)OR$^{70}$, —NR$^{70}$C(O)R$^{70}$, —NR$^{70}$C(S)R$^{70}$, —NR$^{70}$C(O)OR$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$, R$^{70}$, R$^{80}$ and M$^+$ are as previously defined.

In addition to the disclosure herein, in a certain embodiment, a group that is substituted has 1, 2, 3, or 4 substituents, 1, 2, or 3 substituents, 1 or 2 substituents, or 1 substituent.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups specifically contemplated herein are limited to substituted aryl-(substituted aryl)-substituted aryl.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

The term "linker" or "linkage" refers to a linking moiety that connects two groups and has a backbone of 100 atoms or less in length. A linker or linkage may be a covalent bond that connects two groups or a chain of between 1 and 100 atoms in length, for example of 1, 2, 3, 4, 5, 6, 8, 10, 12, 14, 16, 18 or 20 carbon atoms in length, where the linker may be linear, branched, cyclic or a single atom. In certain cases, one, two, three, four or five or more carbon atoms of a linker backbone may be optionally substituted with a sulfur, nitrogen or oxygen heteroatom. The bonds between backbone atoms may be saturated or unsaturated, usually not more than one, two, or three unsaturated bonds will be present in a linker backbone. The linker may include one or more substituent groups, for example with an alkyl, aryl or alkenyl group. A linker may include, without limitations, poly(ethylene glycol); ethers, thioethers, tertiary amines, peptides, alkyls, which may be straight or branched, e.g., methyl, ethyl, n-propyl, 1-methylethyl (iso-propyl), n-butyl, n-pentyl, 1,1-dimethylethyl (t-butyl), and the like. The linker backbone may include a cyclic group, for example, an aryl, a heterocycle or a cycloalkyl group, where 2 or more atoms, e.g., 2, 3 or 4 atoms, of the cyclic group are included in the backbone. A linker may be cleavable or non-cleavable.

The term "synthetic equivalent" refers to a compound that includes a core constituent part of a target molecule to be synthesized that is regarded as the basis of a synthetic procedure. The term refers to a compound that can be utilized as an alternative to a target intermediate or starting material in a synthetic strategy without need for substantively changing the strategy and procedure. It is understood that a synthetic equivalent can be related to the target intermediate or starting material by including the same arrangement of functional groups or precursors thereof, or protected versions thereof, on a fragment of the underlying target scaffold of interest.

"Promoiety" refers to a form of protecting group that, when used to mask a functional group within an active agent, converts the active agent into a prodrug.

The term "pharmaceutically acceptable salt" means a salt which is acceptable for administration to a patient, such as a mammal (salts with counterions having acceptable mammalian safety for a given dosage regime). Such salts can be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, formate, tartrate, besylate, mesylate, acetate, maleate, oxalate, and the like, hydrobromic, hydriodic, sulfuric and phosphoric acid, as well as organic acids such as para-toluenesulfonic, methanesulfonic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate (e.g., 3-hexyne-1,6-dioate), benzoate, chlorobenzoate, methylbenzoate, dinitrobenzoate, hydroxybenzoate, methoxybenzoate, phthalate, terephathalate, sulfonate, xylenesulfonate, phenylacetate, phenylpropionate, phenylbutyrate, citrate, lactate, β-hydroxybutyrate, glycollate, maleate, tartrate, methanesulfonate, propanesulfonates, naphthalene-1-sulfonate, naphthalene-2-sulfonate, mandelate, hippurate, gluconate, lactobionate, and the like salts. In certain specific embodiments, pharmaceutically acceptable acid addition salts include those formed with mineral acids such as hydrochloric acid and hydrobromic acid, and those formed with organic acids such as fumaric acid and maleic acid.

The term "salt thereof" means a compound formed when a proton of an acid is replaced by a cation, such as a metal cation or an organic cation and the like. Where applicable, the salt is a pharmaceutically acceptable salt, although this is not required for salts of intermediate compounds that are not intended for administration to a patient. By way of example, salts of the present compounds include those wherein the compound is protonated by an inorganic or organic acid to form a cation, with the conjugate base of the inorganic or organic acid as the anionic component of the salt.

"Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. When the solvent is water, the solvate formed is a hydrate.

"Stereoisomer" and "stereoisomers" refer to compounds that have same atomic connectivity but different atomic arrangement in space. Stereoisomers include cis-trans isomers, E and Z isomers, enantiomers, and diastereomers.

"Tautomer" refers to alternate forms of a molecule that differ only in electronic bonding of atoms and/or in the position of a proton, such as enol-keto and imine-enamine tautomers, or the tautomeric forms of heteroaryl groups containing a —N═C(H)—NH— ring atom arrangement, such as pyrazoles, imidazoles, benzimidazoles, triazoles, and tetrazoles. A person of ordinary skill in the art would recognize that other tautomeric ring atom arrangements are possible.

It will be appreciated that the term "or a salt or solvate or stereoisomer thereof" is intended to include all permutations of salts, solvates and stereoisomers, such as a solvate of a pharmaceutically acceptable salt of a stereoisomer of subject compound.

"Pharmaceutically effective amount" and "therapeutically effective amount" refer to an amount of a compound sufficient to treat a specified disorder or disease or one or more of its symptoms and/or to prevent the occurrence of the disease or disorder. In reference to tumorigenic proliferative disorders, a pharmaceutically or therapeutically effective amount comprises an amount sufficient to, among other things, cause the tumor to shrink or decrease the growth rate of the tumor.

"Patient" or "subject" refers to human and non-human subjects, especially mammalian subjects.

The term "treating" or "treatment" as used herein means the treating or treatment of a disease or medical condition in a patient, such as a mammal (particularly a human) that includes: (a) preventing the disease or medical condition from occurring, such as, prophylactic treatment of a subject; (b) ameliorating the disease or medical condition, such as, eliminating or causing regression of the disease or medical condition in a patient; (c) suppressing the disease or medical condition, for example by, slowing or arresting the development of the disease or medical condition in a patient; or (d) alleviating a symptom of the disease or medical condition in a patient.

Other definitions of terms may appear throughout the specification.

DETAILED DESCRIPTION

As summarized above, Methods for preparing a variety of ladderane precursors, ladderane compounds and ladderane lipids are provided. The subject methods provide for the preparation of ladderane compounds in multi-gram quantities from commercially available materials. Also provided are methods of preparing a liposome from the ladderane lipids disclosed herein, and compositions thereof. Aspects of the invention include encapsulating one or more cargo moieties in the liposome or compositions thereof and use of the subject liposomal compositions as vehicles in drug delivery, imaging, diagnostics and other medical applications. Aspects of the methods disclosed herein include administering to a subject a liposomal composition comprising a pharmaceutical agent under conditions sufficient to deliver the composition to a site of interest in the subject, and release the pharmaceutical agent from the liposomal composition.

Before the various embodiments are described in greater detail, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

The citation of any publication is for its disclosure prior to the filing date and should not be construed as an admission that the present claims are not entitled to antedate such publication by virtue of prior invention. Further, the dates of publication provided can be different from the actual publication dates which can be independently confirmed.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

All patents and publications, including all sequences disclosed within such patents and publications, referred to herein are expressly incorporated by reference.

In further describing the subject invention, synthetic methods for preparing a variety of ladderane precursors, ladderane compounds and ladderane lipids are described first in greater detail. Next, methods for preparing liposomes of interest are described. Pharmaceutical compositions that find use in the subject methods are also described. Then, methods of interest in which the ladderane liposomes find use are reviewed.

Methods of Ladderane Compound Preparation

As summarized above, the present disclosure provides methods for preparing a variety of ladderane precursors, ladderane compounds and ladderane lipids, including ladderane compounds (2) and (3), ladderane phospholipid [5][3]PC (compound 1) and a variety of other natural and synthetic ladderane lipid compounds. Currently, natural ladderane lipids are poorly studied due to difficulties in obtaining useful amounts of the isolated ladderane lipids. The subject methods provide for synthesis of ladderane compounds including a variety of natural ladderane lipid compounds and new synthetic ladderane lipid compounds. The synthetic approach disclosed herein provides access to a variety of ladderane lipid compounds that exhibit unique and therapeutically significant properties and functions. The synthetic routes provided by the subject methods involve conceptually novel retrosynthetic bond disconnections, and combinations of particular reaction intermediates, particular synthetic methods, particular protecting group chemistries and strategies, and/or particular purification strategies, examples of which are described in length herein. The particular nature and unique sequence of steps with which these bond disconnections are addressed in the subject methods provides for a direct and concise synthesis of ladderane compounds.

As used herein, the term "ladderane lipid" refers to a compound having an underlying amphiphilic lipid core that is mostly hydrophobic (e.g., lipid-like) in structure, but at one end has a region that is hydrophilic (e.g., polar, charged, or a combination of polar and charged groups). The hydrophilic region is referred to as the hydrophilic head group, and the ladderane portion is known as the tail group(s) or ladderane tail. Examples of ladderane lipids include but are not limited to phospholipids, glycolipids, and sphingolipids. Any convenient ladderane lipids, and ladderane precursors or derivatives thereof, can be targeted for synthesis using the subject methods of preparation.

In general terms, the subject methods provide several significant methodological innovations including, but not limited to:

(a) first-in-kind multi-gram synthesis of bicyclohexene ladderane precursor (II);

(b) synthesis of the [5]-ladderane and [3]-ladderane cores; and (c) stereochemical characterization and biophysical interrogation of pure ladderane phospholipids.

In some embodiments, the method is a method of making a ladderane compound of Formula (II) from a compound of formula (I); and a compound of formula (III) from a compound of formula (II):

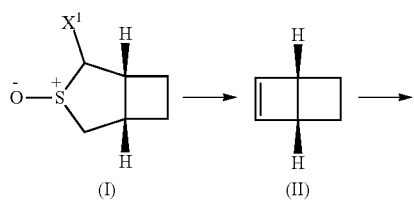

-continued

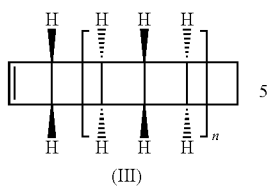
(III)

wherein $X^1$ is a leaving group (e.g., halogen) and n is an integer from 1 to 50, such as 1 to 30, 1 to 20, 1 to 15, 1 to 10, or 1 to 6. In some embodiments of formula (III), n is 1. In some cases of formula (III), n is greater than one, such as 2, 3, 4, 5, 6, 7, 8, 9 or 10. In some cases, n is 1-6. In certain cases, $X^1$ is Br. In certain cases, $X^1$ is Cl.

In some embodiments the method further involves preparing a compound of formula (IV) from the compound of formula (III):

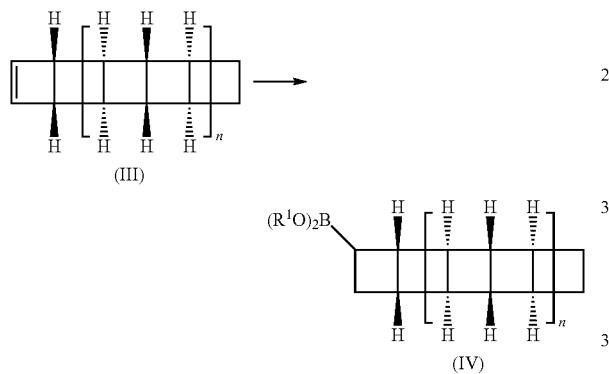

wherein n is an integer from 1 to 50, such as 1 to 30, 1 to 20, 1 to 15, 1 to 10, or 1 to 6; and each $R^1$ is independently an alkyl or a substituted alkyl and are optionally cyclically linked. In some cases of formula (IV), the $R^1$ groups are cyclically linked to form a pinacolboronic ester. In some cases of formula (IV), each $R^1$ is a lower alkyl or a substituted lower alkyl, e.g., a C1-C6 lower alkyl, such as methyl or ethyl. In some cases, the compound of formula (IV) is prepared by enantioselective hydroboration, in 80% or more enantiomeric excess (e.e.), e.g., as described in the experimental section herein, such as 85% ee or greater, 90% ee or greater, or 95% ee or greater. In some cases of formula (IV), n is 1. In some cases of formula (IV), n is greater than 1, such as 2, 3, 4, 5, 6, 7, 8, 9 or 10. In some cases, n is 1-6.

In some embodiments, the method further involves preparing a compound of formula (V) from a compound of formula (IV):

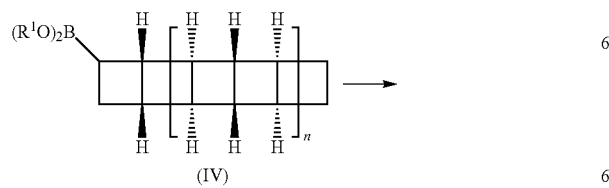
(IV)

-continued

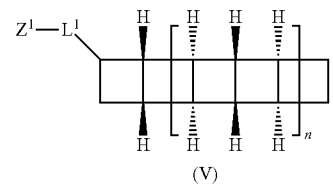
(V)

wherein each $R^1$ is independently an alkyl or a substituted alkyl and are optionally cyclically linked; $L^1$ is a linker; and $Z^1$ is a chemoselective functional group (e.g., as described herein); and n is an integer from 1 to 50, such as 1 to 30, 1 to 20, 1 to 15, 1 to 10, or 1 to 6. In some cases of formula (V), n is 1. In some cases of formula (V), n is greater than 1, such as 2, 3, 4, 5, 6, 7, 8, 9 or 10. In some cases, n is 1-6. In some cases of formula (V), $L^1$ is a linker selected from an aliphatic hydrocarbon that is saturated or unsaturated, linear or branched, substituted or unsubstituted; and $Z^1$ is selected from the group consisting of, carboxylic acid, alcohol, ester, ether, azide, an alkyne, amine, amide and thiol. In certain cases of formula (V), $L^1$ is a linear aliphatic hydrocarbon comprising 4-10 carbons, such as 10, 9, 8, 7, 6, 5 or 4 carbon atoms. In certain cases, $L^1$ is a C2-C10 alkyl or substituted alkyl linker, e.g., a linker having a backbone of 10, 9, 8, 7, 6, 5, 4, 3 or 2 carbon atoms in length. In certain cases of formula (V) $Z^1$ is a carboxylic acid group. In some embodiments, the compound formula (V) has the structure of compound (2):

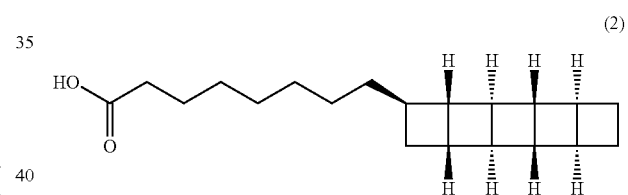

In some embodiments, the method is a method of making a ladderane compound of Formula (VI) from a compound of formula (VII):

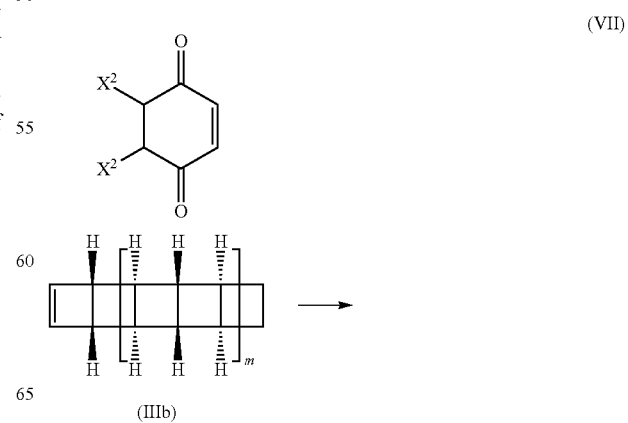
(VII)

(IIIb)

-continued

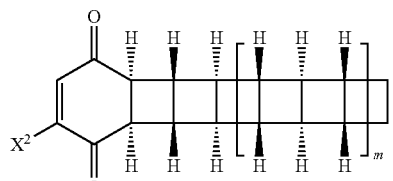

(VI)

wherein $X^2$ is a leaving group (e.g., a halogen); and m is 0 or an integer from 1 to 50, such as 1 to 30, 1 to 20, 1 to 15, 1 to 10, or 1 to 6. In some cases of formulas (VII) and (VI), $X^2$ is bromide. In some cases of formulas (VII) and (VI), $X^2$ is chloride. In some cases, m is 1. In some cases, m is greater than 1, such as 2, 3, 4, 5, 6, 7, 8, 9 or 10. In some cases, m is 1-6. In some cases of formulas (IIIb) and (VI), m is 0 and the method is a method of making a ladderane compound of formula (VIa) from a compound of formula (VII) and a compound of formula (II) (equivalent to formula IIIb when m=0):

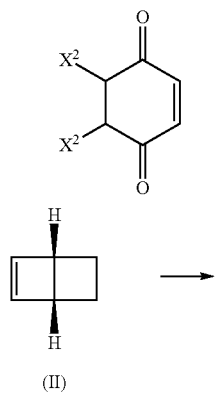

(VII)

(II)

In some embodiments, the method further involves preparing a compound of formula (VIII) from a compound of formula (VI):

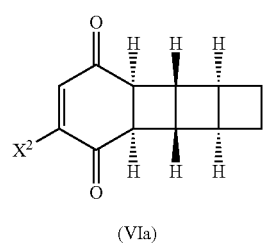

(VIa)

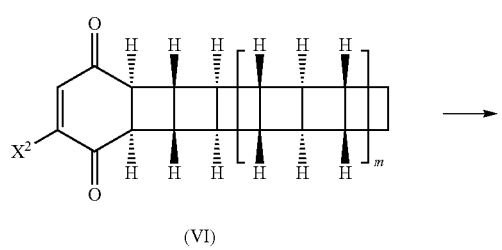

(VI)

-continued

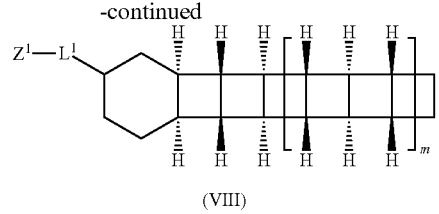

(VIII)

wherein $X^2$ is a leaving group (e.g., a halogen); $L^1$ is a linker (e.g., as described herein); $Z^1$ is a chemoselective group or tag (e.g., as described herein); and m is 0 or an integer from 1 to 50, such as 1 to 30, 1 to 20, 1 to 15, 1 to 10, or 1 to 6. In some cases of formula (VI), $X^2$ is bromide. In some cases of formula (VI), $X^2$ is chloride. In some cases, m is 1. In some cases, m is greater than 1, such as 2, 3, 4, 5, 6, 7, 8, 9 or 10. In some cases, m is 1-6. In some cases of formulas (VI) and (VIII), m is 0 and the method is a method of making a ladderane compound of formula (VIIIa) from a compound of formula (VIa):

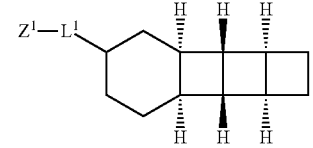

(VIa)

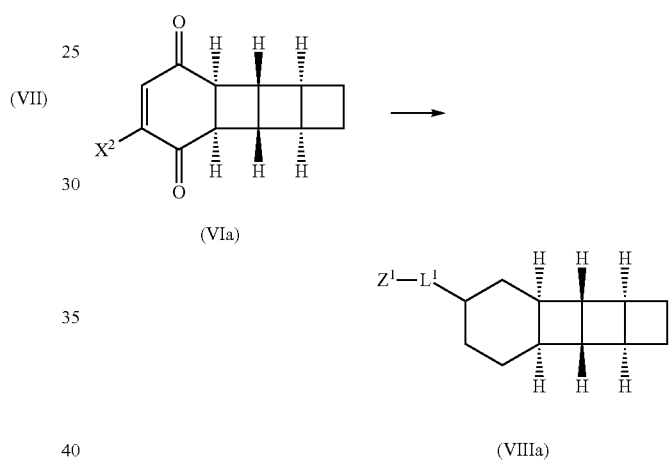

(VIIIa)

In some cases of formula (VIII) or (VIIIa), $L^1$ is a linker selected from an aliphatic hydrocarbon that is saturated or unsaturated, linear or branched, substituted or unsubstituted; and $Z^1$ is selected from the group consisting of, carboxylic acid, alcohol, ester, ether, azide, alkyne, amine, amide and thiol. In certain cases of formula (VIII) or (VIIIa), $L^1$ is a linear aliphatic hydrocarbon comprising 4-10 carbons, such as 10, 9, 8, 7, 6, 5 or 4 carbon atoms. In certain cases $Z^1$ of formula (VIII) or (VIIIa) is an alcohol group. In some embodiments, the compound of formula (VIII) or (VIIIa) has the structure of compound (3):

(3)

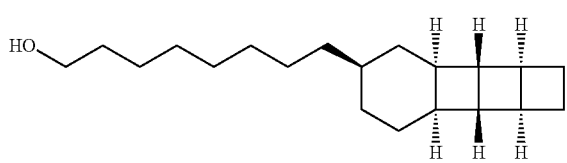

The ladderane precursor compounds can be prepared via a synthetic strategy involving parallel synthesis of a [5]-ladderane tail, such as acid (2) (see e.g., FIG. 1) and [3]-ladderane tails, such as alcohol (3) (see e.g., FIG. 2).

It is understood that the ladderane synthesis methods described herein can also be performed by entering the syntheses at any convenient point in the depicted sequence of steps, e.g., at Step a, Step b, Step c, Step d, Step e, Step f, Step g, Step h, Step i, Step j, Step k, or Step l (e.g., of FIG. 1), or at Step m. Step n, Step o, Step p, Step q, Step r, Step s, or Step t (e.g., of FIG. 2), and progressing to the end of the sequence, thereby bypassing one or more of the earlier steps described. In such cases, any convenient alternative conventional methods can be utilized in preparing as an alternative starting material, one of the intermediate compounds, e.g., one of the intermediate compounds (or an analog thereof) as depicted in FIG. 1 or FIG. 2, or a synthetic equivalent thereof. The subject methods are meant to encompass any sequences and combinations of the subject synthetic steps that lead to the [5]-ladderane tail and [3]-ladderane tail compounds. In some cases, the subject methods lead to ladderane tail compounds of different lengths e.g. ladderanes with 20 cyclobutane rings, 19 cyclobutane rings, 18 cyclobutane rings, 17 cyclobutane rings, 16 cyclobutane rings, 15 cyclobutane rings, 14 cyclobutane rings, 13 cyclobutane rings, 12 cyclobutane rings, 11 cyclobutane rings, 10 cyclobutane rings, 9 cyclobutane rings, 8 cyclobutane rings, 7 cyclobutane rings or 6 cyclobutane rings.

In some cases, a ladderane tail can be prepared according to the subject methods of FIG. 1 beginning at step b. In some cases, the ladderane tail can be prepared according to the subject methods beginning at step c. In some cases, the ladderane tail can be prepared according to the subject methods beginning at step d. In some cases, the ladderane tail can be prepared according to the subject methods beginning at step e. In some cases, the ladderane tail can be prepared according to the subject methods beginning at step f. In some cases, the ladderane tail can be prepared according to the subject methods beginning at step g. In some cases, the ladderane tail can be prepared according to the subject methods beginning at step h. In some cases, the ladderane tail can be prepared according to the subject methods beginning at step i. In some cases, the ladderane tail can be prepared according to the subject methods beginning at step j. In some cases, the ladderane tail can be prepared according to the subject methods beginning at step k. In some cases, the ladderane tail can be prepared according to the subject methods beginning at step l.

In some cases, the a ladderane tail can be prepared according to the subject methods as depicted in FIG. 2 beginning at step n. In some cases, the ladderane tail can be prepared according to the subject methods beginning at step o. In some cases, the ladderane tail can be prepared according to the subject methods beginning at step p. In some cases, the ladderane tail can be prepared according to the subject methods beginning at step q. In some cases, the ladderane tail can be prepared according to the subject methods beginning at step r. In some cases, the ladderane tail can be prepared according to the subject methods beginning at step s. In some cases, the ladderane tail can be prepared according to the subject methods beginning at step t.

A variety of compounds can be utilized as a starting material in the preparation of the ladderane compounds according to the subject methods. It is understood that the methods and procedures described herein can be adapted to utilize any convenient compound as a starting materials, e.g., a synthetic equivalent of any one of the starting materials or intermediates described herein. The subject methods are meant to include methods of preparing the ladderane compounds where one or more (e.g., a, b, c, d, e, f, g, h, i, j, k, l, m, n, o, p, q, r, s, t or more) of the individual steps described herein (e.g., one or more of the steps represented in FIGS. 1 and 2) are adapted and combined to produce the ladderane fragments. In some cases, the strategy allows for variation in protecting groups, and variation in the reagents for carrying out each of the steps. As such, also included are methods of preparing ladderane compounds where any one of the intermediate compounds described herein can be utilized as a starting material, and which can be prepared via any convenient alternative methods. In some cases, the bicyclohexene fragment (II) is prepared from commercially available starting materials, such as (1R, 2S)-cyclobutane-1,2-diyldimethanol (e.g. compound 4, FIG. 1). In some cases the diol, (1R, 2S)-cyclobutane-1,2-diyldimethanol is prepared from the photocycloadduct of maleic anhydride and ethylene:

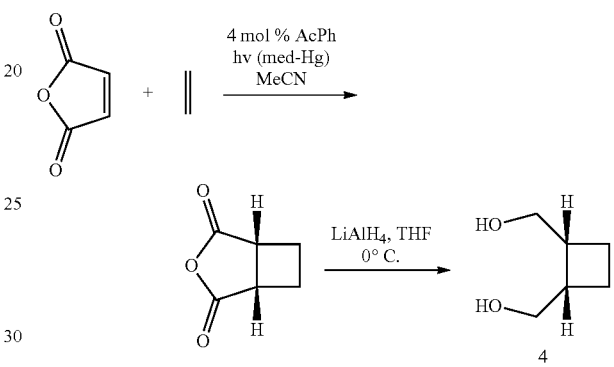

In some cases, the total synthetic step count to complete a [5]-ladderane tail is 12 steps or less from these reagents, such as 11 steps or less, 10 steps or less, 9 steps or less, 8 steps or less, or even less. In some cases, the total synthetic step count to complete a [3]-ladderane tail is 12 steps or less from these reagents, such as 11 steps or less, 10 steps or less, 9 steps or less, 8 steps or less, or even less.

In some embodiments, the method is a method of making a ladderane compound or ladderane lipid of Formula (IX), e.g., from a compound selected from formulae (V) and (VIII):

$$Y^1\text{-}L^2\text{+}L^1\text{-}X^3]_p \qquad (IX)$$

wherein, $X^3$ is selected from the group consisting of:

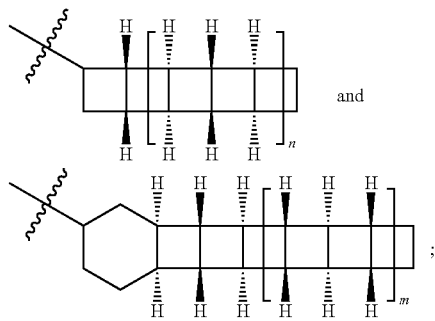

$L^1$ is a first linker; and $L^2$ is an optional second linker; n is 0 or an integer from 1 to 50, such as 1 to 30, 1 to 20, 1 to 15, 1 to 10, or 1 to 6; m is 0 or an integer from 1 to 50, such as 1 to 30, 1 to 20, 1 to 15, 1 to 10, or 1 to 6; p is 1 or 2; and $Y^1$ is a hydrophilic head group. In some cases, m and n are 1. In some cases, n and m are greater than 1, such as 2, 3, 4, 5, 6, 7, 8, 9 or 10. In some cases, n and m are each 1-6.

In some cases, $L^2$ is a branched linker (e.g., a C2-C6 substituted alkyl branched linker). In some case, $L^2$ is a glycerol, polyglycerol, amino glycerol, polyol or peptide. In certain instances, $L^2$ is a glycerol or amino-glycerol linker. An amino-glycerol linker refers to a glycerol linker where one or more of the hydroxyl groups are replaced with an amino group.

In some cases, $L^2$ is an aliphatic hydrocarbon that is saturated or unsaturated, linear or branched, substituted or unsubstituted. In some cases, $L^2$ is a C2-C10 alkyl or substituted alkyl linker.

Any convenient hydrophilic water soluble groups can be adapted for use in the subject lipids. In some cases, $Y^1$ is a charged water soluble group. In some cases, $Y^1$ is a neutral water soluble group. It is understood that charged water soluble groups of interest include basic or acidic groups that can be present in a charged form under aqueous conditions, e.g., at physiological pH. In some cases of formula (IX), the hydrophilic head group $Y^1$ is selected from the group consisting of a phosphate, substituted phosphate, amine, substituted amine, polyamine, polyol, hydroxyl (OH), carboxylate (COO$^-$), sulfate(SO$_4^-$), sulfonate (SO$_3^-$) and carbohydrate. In some cases, $Y^1$ includes a phosphate, thiophosphate, an amine, hydroxyl (OH), phosphonate (—PO(OH)$_2$), carboxylate (—COO$^-$) and sulfonate (—SO$_3^-$). In certain cases of formula (IX), $Y^1$ is a hydrophilic head group of a membrane lipid, such as a phospholipid (glycerophospholipid or sphingolipid) or glycolipid (e.g., sphingolipid) In certain cases of formula (IX), the hydrophilic head group is selected from the group consisting of phosphocholine, phosphoethanolamine, phosphoserine, phosphoinositol, ethylphosphorylcholine, polyethyleneglycol, melamine, glucosamine, trimethylamine.

In some embodiments, the compound of formula (IX) has a structure of formula (X) or (XI):

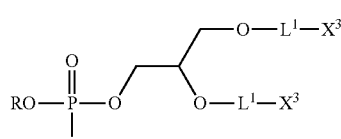
(X)

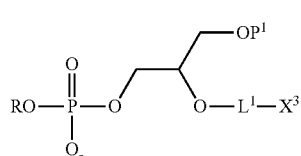
(XI)

and the method comprises, reacting or coupling a ladderane compound of formula (V) or (VIII)

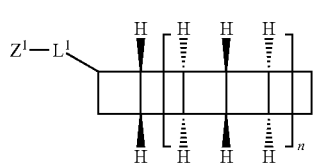
(V)

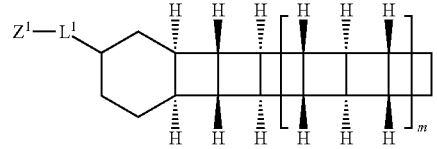
(VIII)

with a glycerol derivative of formula (XII)

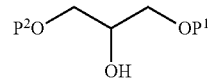
(XII)

and a phosphorylation reagent, wherein $X^3$ is selected from the group consisting of:

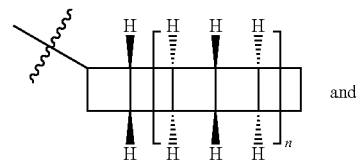
and

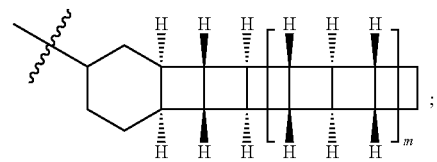
;

$L^1$ is a linker (e.g., as described herein, such as an aliphatic hydrocarbon that is saturated or unsaturated, linear or branched, substituted or unsubstituted; $Z^1$ is selected from the group consisting of, carboxylic acid, alcohol, azide, alkyne, ester, ether, amine, amide, thiol; n is 0 or an integer from 1 to 6; m is 0 or an integer from 1 to 6; $P^1$ is H or a protecting group; and $P^2$ is a protecting group. In some cases of formula (XII), $P^1$ is H. In some cases $P^1$ is a protecting group. In certain cases $P^1$ is a trityl protecting group. In some cases, $P^2$ is a different protecting group from $P^1$. In certain cases, $P^2$ is a p-methoxybenzyl (PMB) protecting group.

In some embodiments both $X^3$ groups in a compound of formula (X) are the same. In some cases of formula (X), both $X^3$ groups have the following structure:

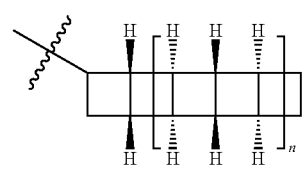

and n is 1. In some cases, n is 2. In some cases, n is 3. In some cases, n is 4. In some cases, n is 5. In some cases, n is 6.

In some cases of formula (X), both $X^3$ groups have the following structure:

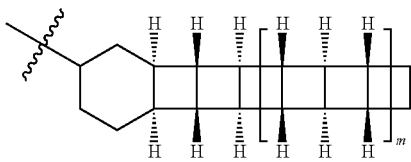

and m is 0. In some cases, m is 1. In some cases, m is 2. In some cases, m is 3. In some cases, m is 4. In some cases, m is 5. In some cases, m is 6.

In some cases the phosphorylation agent is:

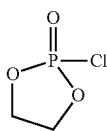

or a synthetic equivalent thereof.

In some embodiments, a compound of formula (X) is prepared from a compound of formula (XI) via a compound of formula (XIII):

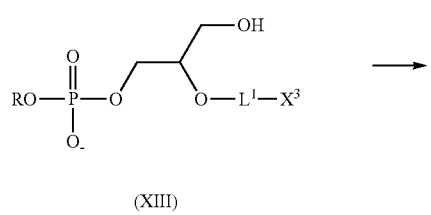

(XIII)

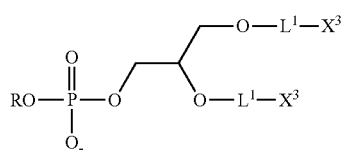

(X)

wherein each $X^3$ group are different. In some cases, one $X^3$ group is

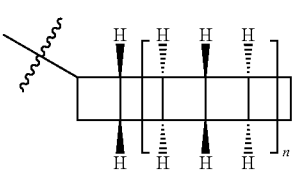

wherein n is 1, and the other $X^3$ group is

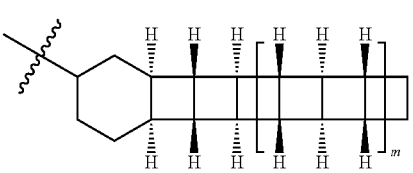

wherein m is 0.

In some embodiments, R in the formulas (X) and (XI) is:

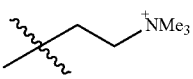

In some embodiments the compound of formula (X) has the structure of compound (1):

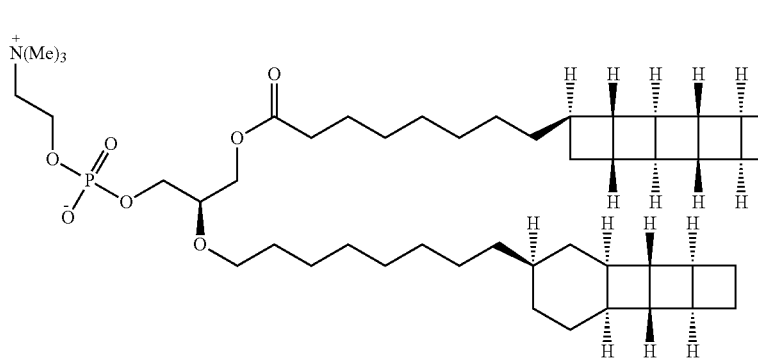

(1)

In some embodiments, the compound of formula (X) has the structure of compound (1a):

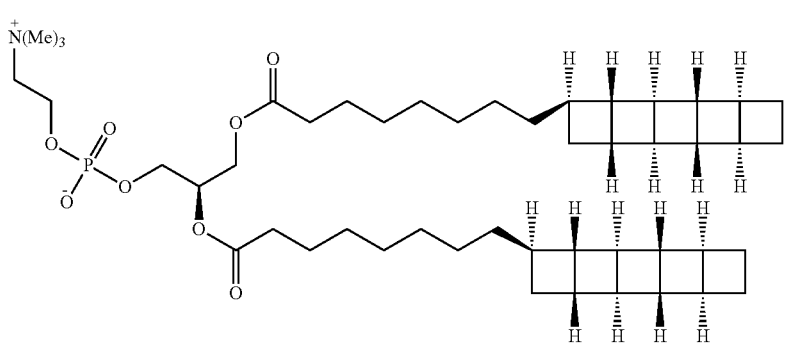

(1a)

In some embodiments, the compound of formula (X) has the structure of compound (1b):

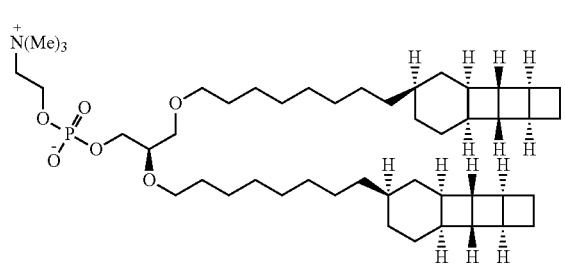

(1b)

In some cases, a ladderane lipid compound of formula (X) or (XI) can be prepared according to the subject methods of FIG. 3 beginning at step 1. In some cases, the ladderane lipid of formula (X) or (XI) can be prepared according to the subject methods beginning at step 2. In some cases, the ladderane lipid of formula (X) or (XI) can be prepared according to the subject methods beginning at step 3. In some cases, the ladderane lipid of formula (X) can be prepared according to the subject methods beginning at step 4. In some cases, the ladderane lipid of formula (X) can be prepared according to the subject methods beginning at step 5. In some cases, the ladderane lipid of formula (X) can be prepared according to the subject methods beginning at step 6. In some cases, the ladderane lipid of formula (X) can be prepared according to the subject methods beginning at step 7.

In some cases, a ladderane lipid compound of formula (X) can be prepared according to the subject methods of FIG. 4 beginning at step 1. In some cases, the ladderane lipid of formula (X) can be prepared according to the subject methods beginning at step 2. In some cases, the ladderane lipid of formula (X) can be prepared according to the subject methods beginning at step 3. In some cases, the ladderane lipid of formula (X) can be prepared according to the subject methods beginning at step 4. In some cases, the ladderane lipid of formula (X) can be prepared according to the subject methods beginning at step 5.

In some cases, a ladderane lipid compound of formula (X) can be prepared according to the subject methods of FIG. 5 beginning at step 1. In some cases, the ladderane lipid of formula (X) can be prepared according to the subject methods beginning at step 2. In some cases, the ladderane lipid of formula (X) can be prepared according to the subject methods beginning at step 3. In some cases, the ladderane lipid of formula (X) can be prepared according to the subject methods beginning at step 4.

Any convenient number of steps can be performed in order to prepare a compound of formula (X) from a starting material of formula (I). In some instances, 20 synthetic steps or less are utilized, such as 15 synthetic steps or less, 14 synthetic steps or less, 13 synthetic steps or less, 12 synthetic steps or less, 11 synthetic steps or less, 10 synthetic steps or less, or even less. As used here, a "synthetic step" refers to a one-pot synthetic procedure from a starting material(s) to produce a product which is isolated at the end of the procedure (e.g., after a workup procedure to remove reagents and impurities) and optionally purified (e.g., via chromatography) and characterized. In certain instances, a single synthetic step can include preparation of an intermediate in situ which is not itself isolated. It is understood that in the synthetic schemes described herein that the arrow indicating starting materials and products can refer to a single synthetic step or multiple synthetic steps.

In some embodiments the methods described herein, further include one or more purification steps. Any method of purification can be utilized in the disclosed methods, including, but not limited to, flash column chromatography, high performance liquid chromatography (HPLC), recrystallization, and distillation.

It is understood that based on the present disclosure, variations of the synthetic strategy, the protecting groups, the reagents and reaction conditions depicted in the figures and purification methods are possible.

Any convenient protection and deprotection steps can be included in the subject methods to temporarily protect a functional group of interest, such as a hydroxyl group or a carboxylic acid.

Ladderane Precursor Compounds

In the subject methods a number of ladderane precursor compounds are generated. In some embodiments, a ladderane precursor, having one of the following structures is prepared:

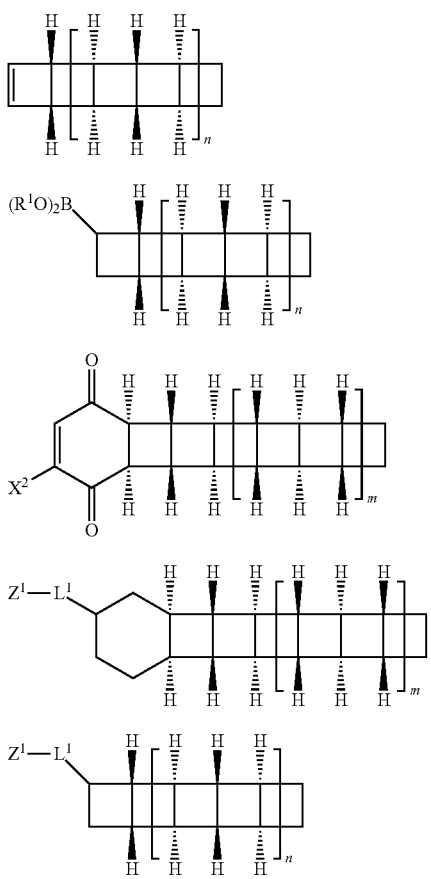

wherein n is an integer from 1 to 20, such as 1 to 10, or 1 to 6; m is 0 or an integer from 1 to 20, such as 1 to 10, or 1 to 6; $R^1$ is independently an alkyl or a substituted alkyl and are optionally cyclically linked; $X^2$ is a halogen; $L^1$ is a linker (e.g., as described herein); and $Z^1$ is a chemoselective group or tag (e.g., as described herein).

In some cases of formula (IV), $R^1$ is a cyclic pinacol ester. In some cases of formula (IV) n is 1. In some cases of formula (IV), n is more than 1, such as 2, 3, 4, 5, or 6.

In some cases of formula (VI), $X^2$ is bromide. In some cases of formula (VI), $X^2$ is chloride. In some cases of formula (VI), $X^2$ is iodide. In some cases of formula (VI), $X^2$ is fluoride. In some cases of formula (VI), m is 0. In some cases of formula (VI), m is more than 0, such as 1, 2, 3, 4, 5, or 6.

In some cases of formula (VIII), m is 0. In some cases of formula (VIII), m is more than 0, such as 1, 2, 3, 4, 5 or 6. In some cases of formula (V), n is 1. In some cases of formula (V), n is more than 1, such as 1, 2, 3, 4, 5, or 6. In some cases of formula (VIII) or (V), $L^1$ is a linker selected from an aliphatic hydrocarbon that is saturated or unsaturated, linear or branched, substituted or unsubstituted; and $Z^1$ is selected from the group consisting of, carboxylic acid, alcohol, ester, ether, azide, alkyne, amine, amide and thiol. In certain cases of formula (VIII) or (V), $L^1$ is a linear aliphatic hydrocarbon comprising 4-10 carbons, such as 10, 9, 8, 7, 6, 5 or 4 carbon atoms. In certain cases of formula (VIII) or (V), $L^1$ is a linear aliphatic hydrocarbon comprising 10 carbon atoms. In certain cases of formula (VIII) or (V), $L^1$ is a linear aliphatic hydrocarbon comprising 9 carbon atoms. In certain cases of formula (VIII) or (V), $L^1$ is a linear aliphatic hydrocarbon comprising 8 carbon atoms. In certain cases of formula (VIII) or (V), $L^1$ is a linear aliphatic hydrocarbon comprising 7 carbon atoms. In certain cases of formula (VIII) or (V), $L^1$ is a linear aliphatic hydrocarbon comprising 6 carbon atoms. In certain cases of formula (VIII) or (V), $L^1$ is a linear aliphatic hydrocarbon comprising 5 carbon atoms. In certain cases of formula (VIII) or (V), $L^1$ is a linear aliphatic hydrocarbon comprising 4 carbon atoms. In certain cases $Z^1$ of formula (VIII) is an alcohol group. In certain cases $Z^1$ of formula (V) is an alcohol group. In certain cases $Z^1$ of formula (VIII) is a carboxylic acid group. In certain cases $Z^1$ of formula (V) is a carboxylic acid group. In certain cases $Z^1$ of formula (VIII) is a protected alcohol group. In certain cases $Z^1$ of formula (V) is a protected alcohol group. In certain cases $Z^1$ of formula (VIII) is a protected carboxylic acid group, or an ester group. In certain cases $Z^1$ of formula (V) is a protected carboxylic acid group or an ester group.

In certain embodiments, the compound of formula (V) has the structure of compound (2):

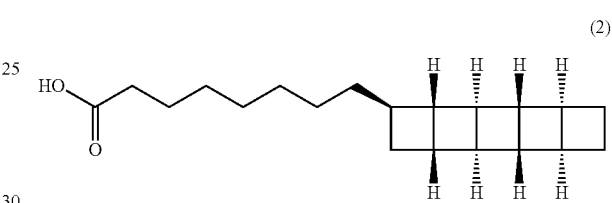

In certain embodiments, the compound of formula (VIII) has the structure of compound (3):

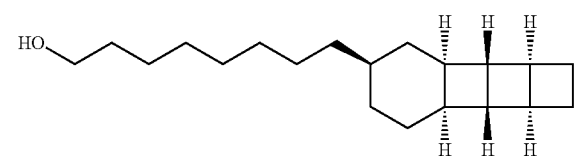 [SMILES: OCCCCCCCC[C@@H]1CC[C@H]2[C@@H](C1)[C@@H]1[C@H]3CC[C@H]3[C@H]21]

Aspects of the present disclosure include ladderane compounds, salts thereof (e.g., pharmaceutically acceptable salts), and/or solvate, hydrate and/or prodrug forms thereof. In addition, it is understood that, in any compound described herein having one or more chiral centers, if an absolute stereochemistry is not expressly indicated, then each center may independently be of R-configuration or S-configuration or a mixture thereof. It will be appreciated that all permutations of salts, solvates, hydrates, prodrugs and stereoisomers are meant to be encompassed by the present disclosure.

In some embodiments, the subject ladderane compounds are provided in the form of pharmaceutically acceptable salts. Compounds containing an amine, imine or nitrogen containing group may be basic in nature and accordingly may react with any number of inorganic and organic acids to form pharmaceutically acceptable acid addition salts.

In some embodiments, the subject compounds, stereoisomers or salts thereof are provided in the form of a solvate (e.g., a hydrate). The term "solvate" as used herein refers to a complex or aggregate formed by one or more molecules of a solute, e.g. a prodrug or a pharmaceutically-acceptable salt thereof, and one or more molecules of a solvent. Such solvates are typically crystalline solids having a substantially fixed molar ratio of solute and solvent. Representative solvents include by way of example, water, methanol, ethanol, isopropanol, acetic acid, and the like. When the solvent is water, the solvate formed is a hydrate.

Methods of Liposome Preparation

As summarized above, the present disclosure provides methods for preparing a liposome from the ladderane lipid compounds disclosed herein. As used herein, the terms "liposome" or "liposomes" are defined as small vesicles composed of amphipathic lipids arranged in spherical bilayers. Liposomes are usually classified as small unilamellar vesicles (SUVs), large unilamellar vesicles (LUVs), giant unilamellar vesicles (GUV), or multi-lamellar vesicles (MLVs). SUVs, LUVs and GUVs, by definition, have only one bilayer, whereas MLVs contain many concentric bilayers. Liposomes may be used to encapsulate various materials, by trapping hydrophilic compounds in the aqueous interior or between bilayers, or by trapping hydrophobic compounds within the bilayer.

Liposomes exhibit a wide variety of characteristics, depending upon their size, composition, and charge. Liposomes may be positive, negative, or neutral in charge, depending on the hydrophilic group. For example, choline-based lipids impart a positive charge, phosphate and sulfate based lipids contribute a negative charge, and glycerol-based lipids and sterols are generally neutral in solution.

In some embodiments, there is provided a method of preparing a liposome, comprising hydrating one or more compounds having a structure selected from (IX), (X) (XI) and (XIII):

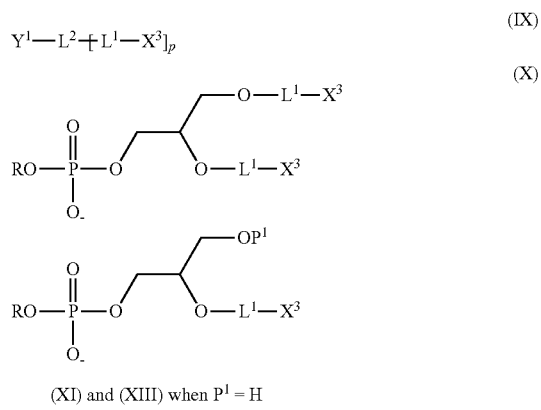

In some cases, hydrating one or more compounds having a structure selected from (IX), (X), (XI) or (XIII) forms giant unilamellar vesicles (GUVs), e.g., via self-assembly of the ladderane compounds. In some cases, hydrating one or more compounds having a structure selected from (IX), (X), (XI) or (XIII) forms small unilamellar vesicles (SUVs). In some cases, hydrating one or more compounds having a structure selected from (IX), (X), (XI) or (XIII) forms large unilamellar vesicles (LUVs). In some embodiments, a compound having a structure selected from (IX), (X), (XI) or (XIII) self-assemble into liposomes with the same bilayer structure characteristic as other known liposomes. In some cases, the subject liposome is prepared using two or more different ladderane compounds.

In some cases, the method of preparing a liposome includes loading with one or more cargo moieties during, or after liposome formation. In certain cases, one or more cargo moieties are selected from the group consisting of an enzyme, a pharmaceutical agent, a plasmid, a polynucleotide, a polypeptide, a sensor, a metal, a polymer, a cell targeting agent, a detectable label and a combination thereof.

In some cases, the liposome is prepared from compound (1). In some cases, the liposome is prepared from compound (1a). In some cases, the liposome is prepared from compound (1b). In some cases, the liposome is prepared from a combination of two or more of the subject compounds, e.g., compound (1), (1a) and/or (1b).

In some cases, the gel to liquid transition temperatures ($T_{gS}$) of a compound of formula (IX), (X), (IX) or (XIII) is below room temperature. In some cases, fluid liposomes of a compound of formula (IX), (X), (IX) or (XIII) are prepared at ambient temperature. In some cases, a compound of formula (IX), (X), (IX) or (XIII) forms GUVs upon gentle hydration. As used herein, "gentle hydration" refers to hydration under mild conditions, such as 40° C. or less, such as 37° C. or less, such as 30° C. or less, such as 25° C. or less. In some cases gentle hydration is achieved at 37° C. In some cases, a compound of formula (IX), (X), (IX) or (XIII) forms GUVs upon hydration at temperatures of 70° C. or more, such as 75° C. or more, such as 80° C. or more, such as 85° C. or more, such as 90° C. or more, such as 95° C. or more, such as 100° C. or even more.

In some cases, a compound of formula (IX), (X), IX) or (XIII) forms GUV at a temperature greater than room temperature, but returns to the gel phase when cooling to room temperature.

In some cases, a compound of formula (IX), (X), (IX) or (XIII) forms SUVs upon gentle hydration and agitation at room temperature followed by extrusion through a polycarbonate membrane. In certain cases, the extrusion is carried out more than 10 times, such as more than 15 times, such as more than 20 times, such as more than 25 times, such as more than 30 times. In certain cases, the extrusion is carried out 31×. In certain cases the polycarbonate membrane has a size of 50 nm. In some cases the polycarbonate membrane has a size of 100 nm. In some cases, the extrusion is carried out through a combination of 100 nm-pore membranes and 50 nm-pore membranes. In some cases the extrusion is carried out through two 100 nm-pore membranes followed by two 50 nm-pore membranes.

In some embodiments a liposome as described herein form supported lipid bilayers (SLBs). In some cases, the liposomes formed are supported on glass.

Pharmaceutical Compositions

As described above, self-assembled liposomes of the present disclosure may be loaded with one or more cargo moieties during or after formation. In some instances, the cargo moiety is a drug or therapeutic agent. Encapsulation of a cargo moiety, such as a drug or active agent inside the liposome may facilitate one or more of: delivery of the cargo moiety to a desired site; formulation of the cargo moiety into a desired formulation; increased stability of the cargo moiety; controlled release of the cargo moiety; delayed release of the cargo moiety; and the like.

In some aspects the composition includes "Pharmaceutically acceptable vehicles" which may be vehicles approved by a regulatory agency of the Federal or a state government or listed in the U.S. Pharmacopeia or other generally recognized pharmacopeia for use in mammals, such as humans. The term "vehicle" refers to a diluent, adjuvant, excipient, or carrier with which a compound of the present disclosure is formulated for administration to a mammal. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents may be used.

Aspects of the present disclosure include compositions that include the liposomes as disclosed herein. The composition may include the liposome and a liquid. In some instances, the composition includes the liposome with a substrate encapsulated within the bilayer, dispersed in the liquid. In some instances, the liquid is a solvent. In some embodiments the liquid is a pharmaceutically acceptable liquid. Any convenient liquid may be used, depending on the desired composition of the liposome.

In one embodiment, there are provided compositions comprising a liposome carrier comprising a ladderane lipid of formula (IX):

$$Y^1\text{-}L^2\text{-}[\text{-}L^1\text{-}X^3]_p \qquad (IX)$$

wherein:

$X^3$ is selected from the group consisting of:

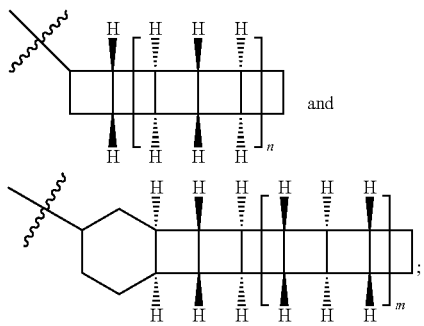

and

;

$L^1$ is a linker selected from an aliphatic hydrocarbon that is saturated or unsaturated, linear or branched, substituted or unsubstituted; and $L^2$ is an optional linker (e.g. a glycerol, polyglycerol, amino glycerol, polyol, peptide);

n is an integer from 1 to 20, such as 1 to 10 or 1 to 6;

m is 0 or an integer from 1 to 20, such as 1 to 10 or 1 to 6;

p is 1 or 2; and $Y^1$ is a hydrophilic head group; and one or more cargo moieties encapsulated in the liposome carrier.

In certain cases, cargo moieties are selected from the group consisting of an enzyme, a therapeutic agent, a plasmid, a polynucleotide, a polypeptide, a sensor, a metal, a polymer, a cell targeting agent, a detectable label and a combination thereof.

Any useful or relevant cargo moiety which can be added to the liposome by any convenient means is of interest. Cargo moieties of interest include, but are not limited to, small drug molecules, fluorescent/radioactive/optical imaging agents, peptides/proteins/enzymes, nucleic acids (siRNA/RNA/DNA/etc.), metal based compounds/catalysts, polymers, site-specific cellular targeting agents (compounds/ligands/antibodies/etc.), etc. for diverse liposome applications such as chemotherapeutic agents, smart adjuvants, gene therapy vectors, biosensors, bioreactors, and so forth. Exemplary cargo moieties of interest include, but are not limited to: Small drug molecules, such as paclitaxel, doxorubicin, daunorubicin, cytarabine, cytosine, arabinoside, vincristine, cisplatin, camphothecin, floxuridine and bryostatin, etc; Peptides, such as pVI (adenovirus lytic domain), TAT (HIV lytic domain), ovalbumin, and NS5A1-31 (Hep C viral membrane anchor), etc.; Proteins, such as GFP, MOMP (chlamydia protein), and EGF/EGFR, antibodies, etc.; Metals and metal ions such as Gold, Silver, Nickel and Copper (bead or catalyst), etc.; and Nucleic Acids, such as DNA, RNA, and siRNA for any convenient gene of interest. In some cases, the cargo moieties are anthracycline chemotherapeutic compounds, such as doxorubicin (DOX).

Any of a number of drugs are suitable for use as a cargo moiety, or can be modified to be rendered suitable for use in the subject liposome compositions. Examples of drugs include small molecule drugs, peptide drugs, protein drugs, enzyme drugs, metal drugs, metal catalyst drugs, and various nucleic acid based drugs.

"Small molecule drug" as used herein refers to a compound, e.g., an organic compound, naturally occurring or synthetic, which exhibits a pharmaceutical activity of interest and which is generally of a molecular weight of 800 Da or less, or 2000 Da or less, but can encompass molecules of up to 5 kDa and can be as large as 10 kDa. A small inorganic molecule refers to a molecule containing no carbon atoms, while a small organic molecule refers to a compound containing at least one carbon atom. "Peptide drug" as used herein refers to amino-acid containing polymeric compounds, and is meant to encompass naturally-occurring and non-naturally-occurring peptides, oligopeptides, cyclic peptides, polypeptides, and proteins, as well as peptide mimetics. The peptide drugs may be obtained by chemical synthesis or be produced from a genetically encoded source (e.g., recombinant source). Peptide drugs can range in molecular weight, and can be from 200 Da to 10 kDa or greater in molecular weight.

In some cases, the drug or therapeutic agent is a cancer chemotherapeutic agent. Cancer chemotherapeutic agents include, but are not limited to, non-peptidic (i.e., non-proteinaceous) compounds that reduce proliferation of cancer cells, and encompass cytotoxic agents and cytostatic agents. Non-limiting examples of chemotherapeutic agents include alkylating agents, nitrosoureas, antimetabolites, antitumor antibiotics, plant (vinca) alkaloids, and steroid hormones. Peptidic compounds can also be used. Suitable cancer chemotherapeutic agents include dolastatin and active analogs and derivatives thereof; and auristatin and active analogs and derivatives thereof (e.g., Monomethyl auristatin D (MMAD), monomethyl auristatin E (MMAE), monomethyl auristatin F (MMAF), and the like). See, e.g., WO 96/33212, WO 96/14856, and U.S. Pat. No. 6,323,315. Suitable cancer chemotherapeutic agents also include maytansinoids and active analogs and derivatives thereof (see, e.g., EP 1391213; and Liu et al (1996) Proc. Natl. Acad. Sci. USA 93:8618-8623); duocarmycins and active analogs and derivatives thereof (e.g., including the synthetic analogues, KW-2189 and CB 1-TM1); and benzodiazepines and active analogs and derivatives thereof (e.g., pyrrolobenzodiazepine (PBD).

Agents that act to reduce cellular proliferation are known in the art and widely used. Such agents include, but are not limited to, alkylating agents, such as nitrogen mustards, nitrosoureas, ethylenimine derivatives, alkyl sulfonates, and triazenes, including, but not limited to, mechlorethamine, cyclophosphamide (Cytoxan™), melphalan (L-sarcolysin), carmustine (BCNU), lomustine (CCNU), semustine (methyl-CCNU), streptozocin, chlorozotocin, uracil mustard, chlormethine, ifosfamide, chlorambucil, pipobroman, triethylenemelamine, triethylenethiophosphoramine, busulfan, dacarbazine, and temozolomide.

Antimetabolite agents include, but are not limited to, folic acid analogs, pyrimidine analogs, purine analogs, and adenosine deaminase inhibitors, including, but not limited to, cytarabine (CYTOSAR-U), cytosine arabinoside, fluorouracil (5-FU), floxuridine (FudR), 6-thioguanine, 6-mercaptopurine (6-MP), pentostatin, 5-fluorouracil (5-FU), methotrexate, 10-propargyl-5,8-dideazafolate (PDDF, CB3717), 5,8-dideazatetrahydrofolic acid (DDATHF), leucovorin, fludarabine phosphate, pentostatine, and gemcitabine.

Suitable natural products and their derivatives, (e.g., vinca alkaloids, antitumor antibiotics, enzymes, lymphokines, and epipodophyllotoxins), include, but are not limited to, Ara-C, paclitaxel (Taxol®), docetaxel (Taxotere®), deoxycoformycin, mitomycin-C, L-asparaginase, azathioprine; brequinar; alkaloids, e.g. vincristine, vinblastine, vinorelbine, vindesine, etc.; podophyllotoxins, e.g. etoposide, teniposide, etc.; antibiotics, e.g. anthracycline, daunorubicin hydrochloride (daunomycin, rubidomycin, cerubidine), idarubicin, doxorubicin, epirubicin and morpholino derivatives, etc.; phenoxizone biscyclopeptides, e.g. dactinomycin; basic glycopeptides, e.g. bleomycin; anthraquinone glycosides, e.g. plicamycin (mithramycin); anthracenediones, e.g. mitoxantrone; azirinopyrrolo indolediones, e.g. mitomycin; macrocyclic immunosuppressants, e.g. cyclosporine, FK-506 (tacrolimus, prograf), rapamycin, etc.; and the like.

Other anti-proliferative cytotoxic agents are navelbene, CPT-11, anastrazole, letrazole, capecitabine, reloxafine, cyclophosphamide, ifosamide, and droloxafine.

Microtubule affecting agents that have antiproliferative activity are also suitable for use and include, but are not limited to, allocolchicine (NSC 406042), Halichondrin B (NSC 609395), colchicine (NSC 757), colchicine derivatives (e.g., NSC 33410), dolstatin 10 (NSC 376128), maytansine (NSC 153858), rhizoxin (NSC 332598), paclitaxel (Taxol®), Taxol® derivatives, docetaxel (Taxotere®), thiocolchicine (NSC 361792), trityl cysterin, vinblastine sulfate, vincristine sulfate, natural and synthetic epothilones including but not limited to, eopthilone A, epothilone B, discodermolide; estramustine, nocodazole, and the like.

Hormone modulators and steroids (including synthetic analogs) that are suitable for use include, but are not limited to, adrenocorticosteroids, e.g. prednisone, dexamethasone, etc.; estrogens and pregestins, e.g. hydroxyprogesterone caproate, medroxyprogesterone acetate, megestrol acetate, estradiol, clomiphene, tamoxifen; etc.; and adrenocortical suppressants, e.g. aminoglutethimide; 17α-ethinylestradiol; diethylstilbestrol, testosterone, fluoxymesterone, dromostanolone propionate, testolactone, methylprednisolone, methyl-testosterone, prednisolone, triamcinolone, chlorotrianisene, hydroxyprogesterone, aminoglutethimide, estramustine, medroxyprogesterone acetate, leuprolide, Flutamide (Drogenil), Toremifene (Fareston), and Zoladex®. Estrogens stimulate proliferation and differentiation; therefore compounds that bind to the estrogen receptor are used to block this activity. Corticosteroids may inhibit T cell proliferation.

Other suitable chemotherapeutic agents include, but are not limited to, metal complexes, e.g. cisplatin (cis-DDP), carboplatin, etc.; ureas, e.g. hydroxyurea; and hydrazines, e.g. N-methylhydrazine; epidphyllotoxin; a topoisomerase inhibitor; procarbazine; mitoxantrone; leucovorin; tegafur; etc. Other anti-proliferative agents of interest include, but are not limited to, immunosuppressants, e.g. mycophenolic acid, thalidomide, desoxyspergualin, azasporine, leflunomide, mizoribine, azaspirane (SKF 105685); Iressa® (ZD 1839, 4-(3-chloro-4-fluorophenylamino)-7-methoxy-6-(3-(4-morpholinyl)propoxy)quinazoline); etc.

Taxanes are suitable for use. "Taxanes" include paclitaxel, as well as any active taxane derivative or pro-drug. "Paclitaxel" (which should be understood herein to include analogues, formulations, and derivatives such as, for example, docetaxel, TAXOL™, TAXOTERE™ (a formulation of docetaxel), 10-desacetyl analogs of paclitaxel and 3'N-desbenzoyl-3'N-t-butoxycarbonyl analogs of paclitaxel) may be readily prepared utilizing techniques known to those skilled in the art (see also WO 94/07882, WO 94/07881, WO 94/07880, WO 94/07876, WO 93/23555, WO 93/10076; U.S. Pat. Nos. 5,294,637; 5,283,253; 5,279,949; 5,274,137; 5,202,448; 5,200,534; 5,229,529; and EP 590,267), or obtained from a variety of commercial sources, including for example, Sigma Chemical Co., St. Louis, Mo. (T7402 from *Taxus brevifolia*; or T-1912 from *Taxus yannanensis*).

Paclitaxel should be understood to refer to not only the common chemically available form of paclitaxel, but analogs and derivatives (e.g., Taxotere™ docetaxel, as noted above) and paclitaxel conjugates (e.g., paclitaxel-PEG, paclitaxel-dextran, or paclitaxel-xylose). Also included within the term "taxane" are a variety of known derivatives, including both hydrophilic derivatives, and hydrophobic derivatives. Taxane derivatives include, but not limited to, galactose and mannose derivatives described in International Patent Application No. WO 99/18113; piperazino and other derivatives described in WO 99/14209; taxane derivatives described in WO 99/09021, WO 98/22451, and U.S. Pat. No. 5,869,680; 6-thio derivatives described in WO 98/28288; sulfenamide derivatives described in U.S. Pat. No. 5,821,263; and taxol derivative described in U.S. Pat. No. 5,415,869. It further includes prodrugs of paclitaxel including, but not limited to, those described in WO 98/58927; WO 98/13059; and U.S. Pat. No. 5,824,701.

In some cases, the composition includes one or more tags on the ladderane lipid of formula (IX). In some cases, the tag is a chemoselective tag or an affinity tag.

In some instances, the tags find use in the selective capture or binding of a secondary agent (e.g., directly and indirectly, e.g., via a secondary covalent reaction or a non-covalent interaction, such as an ionic or hydrophobic interaction). Tags of interest, include but are not limited to, chemoselective tags, affinity tags, and the like.

The terms "chemoselective functional group" and "chemoselective tag" are used interchangeably and refer to functional group that can selectively react or couple with a second compatible functional group on a second molecule to form a covalent bond. Chemoselective functional groups of interest include, but are not limited to, carboxylic acid, alcohol, ester, ether, amine, amide, thiol and maleimide or iodoacetamide, as well as groups that can react with one another via Click chemistry, e.g., azide and alkyne groups (e.g., cyclooctyne groups). Chemoselective functional groups of interest, include, but not limited to, thiols, a phosphine, a maleimide, an alkoxyamine, an aldehyde, ketone, hydrazido, hydrazine, epoxide, maleimide, iodoacetamide or vinyl sulfone, amines, as well as groups that can react with one another via Click chemistry, e.g., azide and alkyne groups (e.g., cyclooctyne groups), sulfur(VI) fluoride exchange chemistry (SuFEX), sulfonyl fluoride, tetrazine, and protected versions thereof, and percursors thereof. In certain embodiments, the chemoselective functional group is an alcohol. In certain embodiments, the chemoselective functional group is a protected alcohol, such as a PMB protected alcohol. In certain embodiments, the chemoselective functional group is a carboxylic acid. In certain embodiments, the chemoselective functional group is a protected carboxylic acid or an ester.

The term "affinity tag" refers to a moiety that can be used to separate a molecule to which the affinity tag is attached from other molecules that do not contain the affinity tag. In certain cases, an "affinity tag" may specifically bind to a binding partner for the affinity tag, thereby facilitating the separation of the molecule to which the affinity tag is attached from other molecules that do not contain the affinity tag. Examples of affinity tags include, but are not limited to, a biotin moiety, digoxygenin, fluorescein, peptide tags and protein tags (e.g., his-tags and the like).

When administered to a mammal, the liposome compositions of the present disclosure and pharmaceutically acceptable vehicles, excipients, or diluents may be sterile. In some instances, an aqueous medium is employed as a vehicle when the subject compound is administered intravenously, such as water, saline solutions, and aqueous dextrose and glycerol solutions.

Pharmaceutical compositions can take the form of capsules, tablets, pills, pellets, lozenges, powders, granules, syrups, elixirs, solutions, suspensions, emulsions, suppositories, or sustained-release formulations thereof, or any other form suitable for administration to a mammal. In some instances, the pharmaceutical compositions are formulated for administration in accordance with routine procedures as a pharmaceutical composition adapted for oral or intravenous administration to humans. Examples of suitable pharmaceutical vehicles and methods for formulation thereof are described in Remington: The Science and Practice of Pharmacy, Alfonso R. Gennaro ed., Mack Publishing Co. Easton, Pa., 19th ed., 1995, Chapters 86, 87, 88, 91, and 92, incorporated herein by reference. The choice of excipient will be determined in part by the particular liposome, as well as by the particular method used to administer the composition. Accordingly, there is a wide variety of suitable formulations of the subject pharmaceutical compositions.

Administration of the subject compositions may be systemic or local. In certain embodiments administration to a mammal will result in systemic release of a liposome composition of the present disclosure (for example, into the bloodstream). Methods of administration may include enteral routes, such as oral, buccal, sublingual, and rectal; topical administration, such as transdermal and intradermal; and parenteral administration. Suitable parenteral routes include injection via a hypodermic needle or catheter, for example, intravenous, intramuscular, subcutaneous, intradermal, intraperitoneal, intraarterial, intraventricular, intrathecal, and intracameral injection and non-injection routes, such as intravaginal rectal, or nasal administration. In certain embodiments, the liposome compositions of the present disclosure are administered subcutaneously. In certain embodiments, the liposome compositions of the present disclosure are administered orally. In certain embodiments, it may be desirable to administer one or more compositions of the present disclosure locally to the area in need of treatment. This may be achieved, for example, by local infusion during surgery, e.g., by injection, by means of a catheter, by means of a suppository, or by means of an implant, said implant being of a porous, non-porous, or gelatinous material, including membranes, such as sialastic membranes, or fibers.

For the treatment of eye disorders, the pharmaceutical formulations of the present disclosure may be administered, e.g., by eye drops, subconjunctival injection, subconjunctival implant, intravitreal injection, intravitreal implant, sub-Tenon's injection or sub-Tenon's implant.

The liposome compositions can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

A subject liposome composition may also be formulated for oral administration. For an oral pharmaceutical formulation, suitable excipients include pharmaceutical grades of carriers such as mannitol, lactose, glucose, sucrose, starch, cellulose, gelatin, magnesium stearate, sodium saccharine, and/or magnesium carbonate. For use in oral liquid formulations, the composition may be prepared as a solution, suspension, emulsion, or syrup, being supplied either in solid or liquid form suitable for hydration in an aqueous carrier, such as, for example, aqueous saline, aqueous dextrose, glycerol, or ethanol, in some cases water or normal saline. If desired, the composition may also contain minor amounts of non-toxic auxiliary substances such as wetting agents, emulsifying agents, or buffers. In some embodiments, formulations suitable for oral administration can include (a) liquid solutions, such as an effective amount of the compound dissolved in diluents, such as water, or saline; (b) capsules, sachets or tablets, each containing a predetermined amount of the active ingredient, as solids or granules; (c) suspensions in an appropriate liquid; and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can include the active ingredient in a flavor, usually sucrose and acacia or tragacanth, as well as pastilles including the active ingredient in an inert base, such as gelatin and glycerin, or sucrose and acacia, emulsions, gels, and the like containing, in addition to the active ingredient, such excipients as are described herein.

In some embodiments, formulations suitable for parenteral administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may include the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of liposome composition of the present disclosure calculated in an amount sufficient to produce the desired effect in association with a pharmaceutically acceptable diluent, carrier or vehicle. The specifications for the novel unit dosage forms of the present disclosure depend on the particular compound employed and the effect to be achieved, and the pharmacodynamics associated with each compound in the host. In pharmaceutical dosage forms, the compounds may be administered in the form of a free base, their pharmaceutically acceptable salts, or they may also be used alone or in appropriate association, as well as in combination, with other pharmaceutically active compounds.

Dose levels can vary as a function of the specific liposome compositions, the nature of the delivery vehicle, and the like. Desired dosages for a given composition are readily determinable by a variety of means. The dose administered to an animal, particularly a human, in the context of the present disclosure should be sufficient to effect a prophylactic or therapeutic response in the animal over a reasonable time frame, e.g., as described in greater detail herein. Dosage will depend on a variety of factors including the strength of the particular compound employed, the condition of the animal, and the body weight of the animal, as well as the severity of the illness and the stage of the disease. The size of the dose will also be determined by the existence, nature, and extent of any adverse side-effects that might accompany the administration of a particular compound.

Methods of Use

Also provided are methods of using the subject liposome compositions as vehicles in drug delivery, imaging, diagnostics and other medical applications. Aspects of the methods disclosed herein include administering to a subject a liposomal composition as disclosed herein comprising a pharmaceutical agent under conditions sufficient to deliver the liposomal composition to a site of interest in the subject, and release the pharmaceutical agent from the liposomal composition at the site of interest. In some cases, the site of interest is a tumor. In certain cases, the pharmaceutical agent is a small drug molecule or a peptide drug as described herein. In certain cases, the pharmaceutical agent is a chemotherapy agent. In certain cases, the chemotherapy agent is selected from the group, paclitaxel, doxorubicin, daunorubicin, cytarabine, cytosine, arabinoside, vincristine, cisplatin, camptrothecin and floxuridine.

In contrast to traditional liposome formulations that often leak drugs, ladderane lipid-based membranes are dense and comparatively more impermeable to small molecules which makes them ideal vehicles to selectively penetrate cells for medical applications and in nanofabrication.

In some cases, the liposome compositions may provide for the site specific delivery of a pharmaceutical or therapeutic agent of interest at a desired therapeutic dosage. In certain cases, delivery may be achieved over an extended period of time.

The method of use may be a method of delivering a pharmaceutical agent to a cell in vitro and in vivo. In some embodiments, the method includes, contacting a cell with a liposomal composition (e.g., as described herein), under conditions in which the pharmaceutical agent is released and diffuses from the liposome composition. In some instances, the liposomal composition includes a plurality of pharmaceutical agents (e.g., 2 or more, 3 or more, 4 or more, 5 or more, 6 or more, 7 or more, 8 or more, 9 or more, 10 or more, pharmaceutical agents, etc.). Any convenient pharmaceutical agents may be delivered according to the subject methods. Pharmaceutical agents of interest include, but are not limited to, those convenient cargo moieties described herein. In certain instances, the pharmaceutical agent includes, but are not limited to, an imaging agent, a plasmid, a polynucleotide, a polypeptide, a chemotherapeutic agent, a pro-drug, or combination thereof. In certain instances, the pharmaceutical agent is a therapeutic agent. In certain instances, the pharmaceutical agent is an imaging agent. In some cases, the therapeutic agents are released by the liposomal composition without contact with an external stimulus, but rather through a degradation or dissociation process in vitro or in vivo. In some embodiments, release of desired pharmaceutical agent results in its activation for biological activity, e.g. pro-drug delivery. A variety of intracellular conditions of target cells may be adapted for use in the subject methods and compositions.

In certain embodiments, the liposomal composition provides for a multi-layered pharmaceutical agent release. In some cases, the pharmaceutical agent is attached to the liposome via two or more different types of tags, and/or binding interactions. For example, a quick release of drug may be achieved using a pH sensitive tag or connection, then a slower enzymatic cleavage may provide for further sustained drug release from the liposome, and finally in vivo vault degradation may provide for a further slower release of drug from the liposome. Any convenient configurations of liposomal composition, and cargo moieties may be selected to provide for a multiple pharmaceutical agent release mechanisms and drug delivery over an extended period of time. In additional embodiments, the delivered cargo can consist of an inactive pro-drug entity(ies) which becomes biologically activated upon release from the liposomal composition. In further embodiments, release and activation of pro-drug cargo from the vault particle may be dependent upon delivery to appropriate target cells, tissues, organs, etc. which contain the necessary activating agent as a means to limit pro-drug activation to desired cellular locations. The cell may be in a biological sample. The term "sample" as used herein relates to a material or mixture of materials, typically, although not necessarily, in liquid form, containing one or more analytes of interest. In one embodiment, the term as used in its broadest sense, refers to any plant, animal or bacterial material containing cells or producing cellular metabolites, such as, for example, tissue or fluid isolated from an individual (including without limitation plasma, serum, cerebrospinal fluid, lymph, tears, saliva and tissue sections) or from in vitro cell culture constituents, as well as samples from the environment. In some cases, the sample is derived from a human. The term "sample" may also refer to a "biological sample".

The term "a biological sample" refers to a whole organism or a subset of its tissues, cells or component parts (e.g. body fluids, including but not limited to blood, mucus, lymphatic fluid, synovial fluid, cerebrospinal fluid, saliva, amniotic fluid, amniotic cord blood, urine, vaginal fluid and semen). A "biological sample" can also refer to a homogenate, lysate or extract prepared from a whole organism or a subset of its tissues, cells or component parts, or a fraction or portion thereof, including but not limited to, for example, plasma, serum, spinal fluid, lymph fluid, the external sections of the skin, respiratory, intestinal, and genitourinary tracts, tears, saliva, milk, blood cells, tumors, organs. In certain embodiments, the sample has been removed from an animal or plant. Biological samples of the invention include cells. The term "cells" is used in its conventional sense to refer to the basic structural unit of living organisms, both eukaryotic and prokaryotic, having at least genetic material and a cell membrane. In certain embodiments, cells include prokaryotic cells, such as from bacteria. In other embodiments, cells include eukaryotic cells, such as cells obtained from biological samples from animals, plants or fungi.

In some embodiments, the cell is in vivo and the pharmaceutical agents are released and/or diffuse from the liposome composition to achieve immediate, delayed, or constant therapeutic level in the cell over a suitable period of time, e.g., an extended period of time suitable for achieving a therapeutic result.

The pharmaceutical agents are included in the liposomal composition in an amount sufficient to deliver to the individual a therapeutically effective amount of the pharmaceutical agent to treat, for example, abnormal cell proliferation in vivo, without causing serious toxic effects in the individual being treated. It is to be understood that for any particular individual, specific dosage regimens can be adjusted over time according to the individual need and the professional judgment of the person administering or supervising the administration of the liposomal compositions. The liposomal compositions may be administered at once, or may be divided into a number of smaller doses to be administered at varying intervals of time.

In one embodiment, the liposomal compositions of the present disclosure find use in liposomal chemotherapy in mammalian subjects. For example, representative cancer conditions and cell types against which the liposomal compositions of the present disclosure may be useful include melanoma, myeloma, chronic lymphocytic leukemia (CLL), AIDS-related lymphoma, non-Hodgkin's lymphoma, colorectal cancer, renal cancer, prostate cancer, cancers of the head, neck, stomach, esophagus, anus, or cervix, ovarian cancer, breast cancer, peritoneal cancer, and non-small cell lung cancer.

In some cases the subject to be treated is a human subject. In some cases the subject to be treated is a cancer patient. In certain cases, the subject is a cancer patient whose candidate treatment failed in the clinic. In some cases, the candidate treatment failed in the clinic due to high toxicity.

Utility

The ladderane compounds, ladderane lipids and liposomal compositions as described herein along with methods of preparing the same may find use in a variety of applications, including therapeutic, diagnostic and research applications, particularly in medical applications which are plagued by toxicity and side effects.

The subject methods of ladderane precursor synthesis provide a sustainable, scalable, reproducible, and economical way to obtain large quantities of a variety of ladderane compounds which can be subsequently used in the synthesis of ladderane lipid compounds and liposome formation for encapsulating a pharmaceutical agent for controlled release in various therapies.

The subject methods also allow the synthesis of naturally occurring ladderane phospholipids, enabling the determination of their absolute stereochemistry and investigation of their properties in monolayers and bilayers.

The subject methods and compositions provide the ability to deliver a therapeutic agent to a site of interest and selectively release the therapeutic agent at the site of interest, thereby shielding the healthy tissues from any side effects associated with the therapeutic agent.

The subject liposomal compositions provide liposomes with tightly packed ladderane lipid tails, which both avoid interactions with lipophilic proteins (such as opsonizing proteins that signal uptake by the reticuloendothelial system (RES)) and block drug leakage. Such liposomal compositions provide for improved methods in liposomal therapy, such as chemotherapy. This holds the potential for an approach towards cancer chemotherapy which suffers from toxicity and side effects associated with the chemotherapeutic agents. In treatment, the subject liposomal compositions can be used to encapsulate a chemotherapeutic agent so that healthy tissues may be shielded from the agent. In doing so, the agent may be kept in circulation for an extended time and released selectively at the appropriate site (e.g. the tumor).

Cancer is the leading cause of death in developed countries and a rapidly rising problem in others. Cancer chemotherapy is one of the most promising approaches to addressing this global problem.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for.

Example 1

Synthetic Strategy

Exemplary [5]-ladderane compounds disclosed herein contain 5 cyclobutane units, a linear alkyl component ending in a carboxylic acid group and 9 chiral centres. Exemplary [3]-ladderane compounds disclosed herein contain 3 cyclobutane units, a linear alkyl component ending in an alcohol group and 7 chiral centres. The synthesis of ladderane compounds described herein is accomplished through first setting up the cyclobutane containing core as a key intermediate, then installing the linear alkyl component, which allows access to ladderane compounds of any chain length from an advanced late stage intermediate.

The chemical starting reagents for the synthesis of the [5]-ladderane compound in some cases is (1R, 2S)-cyclobutane-1,2-diyldimethanol (e.g. compound 4, FIG. 1). In some cases the diol, (1R, 2S)-cyclobutane-1,2-diyldimethanol is prepared from the photocycloadduct of maleic anhydride and ethylene:

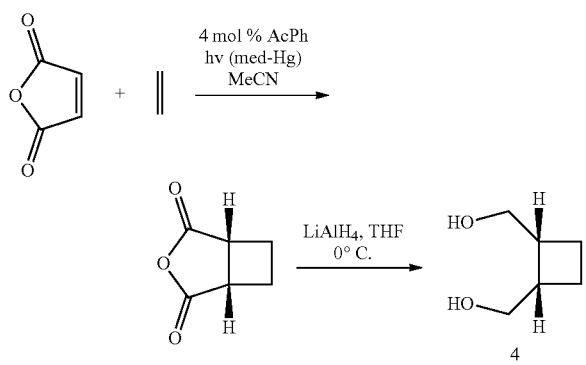

(See FIG. 1 for depiction of the following steps):

Step a) mesylation of 3(1R, 2S)-cyclobutane-1,2-diyldimethanol (compound 4) provides a dimesylate derivative in high yield.

Step b) the dimesylate derivative from step a) is converted to the corresponding sulfoxide derivative by treatment with sodium sulfide and hydrogen peroxide. A 5:1 mixture of diastereomers is formed in this step which are separable by chromatrography. However, the mixture is inconsequential as both diastereomers perform the same following reaction.

Step c) the sulfoxide derivative is converted to α-chlorosulfoxide (compound 5) by treatment with sulfuryl chloride. Compound 5 was isolated as an inseparable mixture of chloride epimers that were carried together into the subsequent reaction. It was observed that compound 5 decomposed spontaneously if stored at room temperature for more than 12 hours. However, no decomposition was observed over a year of storage under nitrogen at −20° C.

Step d) treatment of α-chlorosulfoxide (5) with potassium tert-butoxide effected an atypical sulfoxide Ramberg-Backland ring contraction providing bicyclohexene (compound II). The resulting bicyclohexene (compound II) was purified by distillation to provide large quantities of (II).

Step e) the [5]-ladderane pentacycle (compound 6) was obtained by [2+2] photocycloaddition of compound II with copper(I) triflate as a catalyst and benzene as the solvent below 0° C. Initial attempts to achieve dimerization of bicyclohexene II to compound 6 under typical conditions were plagued by the thermal conversation of compound II to 1,3-cyclohexadiene. This undesired side reaction could be slowed by conducting the reaction at temperatures below 0° C. The reaction proceeds in benzene, which is actually frozen under the reaction conditions.

Step f) a C—H chlorination is carried out by treatment of compound 6 with catalytic tetramesitylporphyrinatomanganese(III) chloride to provide an intermediate chloro-ladderane, along with recovered compound 6.

Step g) an elimination reaction with potassium tert-butoxide furnishes olefin (compound 7).

Step h) an enantioselective hydroboration reaction desymmetrized achiral olefin 7 to provide pinacolboronic ester (compound 8).

Step i) a Zweifel olefination was employed to install the 8-carbon alkyl chain.

Step j) a TBS deprotection reaction gave alkene (compound 9) in high combined yield over steps i) and j).

Step k) a hydrogenation reaction with Ra—Ni afforded a crystalline [5]-ladderanol intermediate.

Step l) Jones oxidation of the [5]-ladderanol intermediate completes the synthesis of [5]-ladderane compound 2.

It is understood that that method described above can be performed by entering the synthesis at any convenient point in the sequence of steps, e.g., at Step a, Step b, Step c, Step d, Step e, Step f, Step g, Step h, Step i, Step j, Step k or Step l and progressing to the end of the sequence, thereby bypassing one or more of the first steps described. In such cases, any convenient alternative conventional methods can be utilized in preparing as a starting material, one of the intermediate compounds, e.g., one of the intermediate compounds (or an analog thereof) depicted in FIG. 1. In some cases, the [5]-ladderane compound 2 can be prepared according to the subject methods beginning at step b. In some cases, the [5]-ladderane compound 2 can be prepared according to the subject methods beginning at step c. In some cases, the [5]-ladderane compound 2 can be prepared according to the subject methods beginning at step d. In some cases, the [5]-ladderane compound 2 can be prepared according to the subject methods beginning at step d. In some cases, the [5]-ladderane compound 2 can be prepared according to the subject methods beginning at step e. In some cases, the [5]-ladderane compound 2 can be prepared according to the subject methods beginning at step f. In some cases, the [5]-ladderane compound 2 can be prepared according to the subject methods beginning at step g. In some cases, the [5]-ladderane compound 2 can be prepared according to the subject methods beginning at step h. In some cases, the [5]-ladderane compound 2 can be prepared according to the subject methods beginning at step i. In some cases, the [5]-ladderane compound 2 can be prepared according to the subject methods beginning at step j. In some cases, the [5]-ladderane compound 2 can be prepared according to the subject methods beginning at step k. In some cases, the [5]-ladderane compound 2 can be prepared according to the subject methods beginning at step l.

The chemical starting reagents for the synthesis of a [3]-ladderane compound are the commercially available dibromodiol (compound 10) and bicyclohexene II. Racemic dibromodiol could be easily enantioenriched via lipase resolution to provide (−)-dibromodiol. The synthetic sequence of a [3]-ladderane compound is as follows (see FIG. 2 which depicts the following steps):

Step m) an oxidation of dibromodiol (compound 10) to afford dibromobenzoquinone (compound 11). The dibromobenzoquinone intermediate served as a high-yielding [2+2] partner for the photocycloaddition with bicyclohexene II, it also allowed for the relay of stereochemistry into the [3]-ladderane core.

Step n) and o) a photocycloaddition between compound 11 and bicyclohexene II provided dibromodiketone (compound 12), which upon treatment with pyridine underwent selective elimination to diketo alkene (compound 13). Slight erosion of enantiopurity was observed in this step.

Step p) Installation of the linear alkyl chain was accomplished by addition of an alkylzinc iodide reagent to compound 13 to provide diketone 14.

Step q) and r) a double Wolff-Kishner type reduction of compound 14. Intermediate bis-hydrazone (compound 15) was prepared by treatment of diketone 14 with hydrazine. Upon attempting the double Wolff-Kishner reduction of intermediate 15, it was discovered that the apparent 2-electron oxidation and release of two molecules of dinitrogen could deliver 1,3-cyclohexadine 16. After some optimization it was found that Cu-TMEDA was an effective oxidant to obtain to 1,3-cyclohexadiene 16 in modest yield.

Step s) and t) a hydrogenation reaction of diene 16. The diene 16 underwent diastereoselective hydrogenation under action of Crabtree's catalyst. Deprotection of the PMB completes the synthesis of [3]-ladderane compound 3.

It is understood that that method described above can be performed by entering the synthesis at any convenient point in the sequence of steps, e.g., at Step m, Step n, Step o, Step p, Step q, Step r, Step s or Step t, and progressing to the end of the sequence, thereby bypassing one or more of the first steps described. In such cases, any convenient alternative conventional methods can be utilized in preparing as a starting material, one of the intermediate compounds, e.g., one of the intermediate compounds (or an analog thereof) depicted in FIG. 2. In some cases, the [3]-ladderane compound 3 can be prepared according to the subject methods beginning at step n. In some cases, the [3]-ladderane compound 3 can be prepared according to the subject methods beginning at step o. In some cases, the [3]-ladderane compound 3 can be prepared according to the subject methods beginning at step p. In some cases, the [3]-ladderane compound 3 can be prepared according to the subject methods beginning at step q. In some cases, the [3]-ladderane compound 3 can be prepared according to the subject methods beginning at step r. In some cases, the [3]-ladderane compound 3 can be prepared according to the subject methods beginning at step s. In some cases, the [3]-ladderane compound 3 can be prepared according to the subject methods beginning at step t.

Exemplary ladderane lipids disclosed herein contain either [5]-ladderane compounds, [3]-ladderane compounds or a combination of [5]-ladderane and [3]-ladderane compounds. Exemplary ladderane lipids disclosed herein are based on a phosphatidylcholine (PC) core. A PC core containing two [5]-ladderane compounds of formula 2 is sometimes referred to herein as "[5][5]PC". A PC core containing two [3]-ladderane compounds of formula 3 is sometimes referred to herein as "[3][3]PC". A PC core containing a [3]-ladderane compound of formula 3 and a [5]-ladderane compound of formula 2 is sometimes referred to herein as "[5][3]PC. Exemplary ladderane lipids disclosed herein contain a choline head group, a glycerophosphoric acid, and ladderane tail groups.

The synthesis of PC ladderane lipids described herein is accomplished through alkylation and/or esterification of an enantiopure glycerol derivative followed by installation of the phosphocholine head group.

Synthetic sequences to [5][3]PC, [5][5]PC and [3][3]PC are outlined in FIG. 3, FIG. 4 and FIG. 5, respectively.

With reference to FIG. 3, the synthesis begins with a ladderane compound of formula 3, which is mesylated to provide compound 17, which is then reacted with a di-protected enantiopure glycerol derivative, followed by selective deprotection of the trityl group to afford alcohol 19. Esterification with a ladderane compound of formula 2 followed by subsequent PMB deprotection gave the mixed ether-ester glycerol 21. Installation of the phosphocholine head group completed the synthesis of [5][3]PC (compound 1).

With reference to FIG. 4, the synthesis begins with a double esterification of an enantiopure glycerol derivative with ladderane compound 2 to give the PMB protected derivative 24. Deprotection of the PMB group, followed by installation of the phosphocholine head group completed the synthesis of [5][5]PC (compound 1a).

With reference to FIG. 5, the synthesis begins with a double alkylation of an enantiopure glycerol derivative with ladderane compound 17 to give the PMB protected derivative 22. Deprotection of the PMB group, followed by installation of the phosphocholine head group completed the synthesis of [3][3]PC (compound 1b).

Example 1: Exemplary Synthetic Procedures

[5]-ladderane compounds, [3]-ladderane compounds and ladderane phospholipids [5][3]PC, [5][5]PC and [3][3]PC were synthesized according to the procedures disclosed in 62/381,857, and Mercer, Jaron A. M.; Cohen, Carolyn M.; Shuken, Steven R.; Wagner, Anna M.; Smith, Myles W.; Moss, Frank R.; Smith, Matthew D.; Vahala, Riku; Gonzalez-Martinez, Alejandro (2016 Dec. 14). "Chemical Synthesis and Self-Assembly of a Ladderane Phospholipid". *Journal of the American Chemical Society.* 138 (49): 15845-15848, which is incorporated herein in its entirety.

Example 2: Exemplary Self-Assembly of Ladderane Phospholipids into Liposomes

In was found that after incorporation of 0.1 mol % Texas Red-DHPE and gentle hydration, [3][3]PC (compound 1b) and [5][3]PC (compound 1) formed giant unilamellar vesicles (GUVs) (FIG. 6A and FIG. 6B) with homogeneous incorporation of dye, suggesting a fluid bilayer. Formation of visible giant vesicles from [5][5]PC (compound 1a) required heating during hydration; upon cooling and visualization, it was observed objects qualitatively similar to cooled GUVs of lipids whose transition temperatures are above room temperature (FIG. 6C). A 1:1 mixture of [3][3] PC and [5][5]PC formed giant vesicles with visible gel/liquid phase separation (FIG. 6D), as would be expected for mixtures of conventional straight-chain phospholipids with $T_m$s above and below room temperature.

Hydration and agitation of [3][3]PC or [5][3]PC at room temperature followed by extrusion 31× through a 50 nm-pore polycarbonate membrane resulted in the formation of nanostructures of similar scattering intensity and polydispersity to small unilamellar vesicles (SUVs) formed from common phosphatidylcholines (PCs) measured by dynamic light scattering (DLS), albeit of about 20% larger size. The typical SUV size could be achieved by extruding through two 100 nm-pore membranes followed by two 50 nm-pore membranes.

Both SUVs and GUVs formed from ladderane PCs also ruptured on glass to form supported lipid bilayers (SLBs) that appeared identical to SLBs formed from vesicles composed of straight-chain PCs (see below).

As ladderane PCs appeared to have analogous self-assembly properties to straight-chain PCs, i.e. the formation of either liquid- or gel-phase lipid bilayers using standard methods developed for straight-chain PCs, it was deduced that traditional biophysical techniques were viable for studies on ladderane PCs.

The facile preparation of vesicles, monolayers and supported bilayers of [3][3]PC and [5][3]PC was not anticipated. The fact that lipids so structurally different from straight-chain phospholipids self-assemble in the same way indicates that many other derivatives may be counterintuitively capable of these same modes of self-assembly.

Example 3: Differential Scanning Calorimetry (DSC)

Lipid films with 1:1 ethylene glycol:phosphate buffer were hydrated and differential scanning calorimetry (DSC) was performed to measure the transition temperatures $T_m$ of the aqueous dispersions. A single transition between −40 and 80° C. was observed for each ladderane PC dispersion. In agreement with the self-assembly experiments above, [3][3] PC and [5][3]PC have $T_m$s below room temperature and the $T_m$ of [5][5]PC is above room temperature (FIG. 6E, entries 1-3).

The effect of removing one C—C bond from the [5]-ladderane in [5][5]PC to make the [3]-ladderane in [5][3]PC (FIG. 7, entries 2 and 3) mirrors the effect of introducing an unsaturation to DSPC to make SOPC (FIG. 7, entries 5 and 7). [5][5]PC, whose tails each contain 20 Cs, has about the same $T_m$ as 20:0 PC, whereas [3][3]PC has about the same $T_m$ as the unsaturated lipid 22:1 PC. These results suggest that [5]-ladderane motifs experience stabilizing packing interactions in the gel phase similar to saturated straight chains of the same number of carbons; the [3]-ladderane structure, as in the case of a cis-unsaturation, counteracts this stabilization. The higher $T_m$ of [3][3]PC over [5][3]PC (FIG. 7, entries 1 and 2) suggests that the [3]-ladderane structure may participate in homologous packing that is disrupted by the presence of [5]-ladderane tails.

Structural Model of the Ladderane Lipid Bilayer

The permeability characteristics and biophysical data can be used to build a qualitative model for ladderane bilayers. Ladderane PCs can self-assemble into membranes with the same bilayer structure characteristic of other PCs. Extrapolating from monolayers at the air-water interface to bilayers, a ladderane PC molecule likely occupies approximately 50% less lateral area than a conventional PC such as POPC or DOPC, while still existing in a fluid phase at room temperature. Considering this lateral packing, the close proximity of carbon atoms in cyclobutane groups, and the conformational rigidity of ladderanes, the hydrocarbon density is likely much higher within the bilayer than in bilayers of straight chain PCs, as is predicted by molecular dynamics simulations (Chaban V V, Nielsen M B, Kopec W, Khandelia H (2014) Insights into the role of cyclic ladderane lipids in bacteria from computer simulations. *Chem Phys Lipids* 181: 76-82.).

One important point from the transition temperatures is that [3]-ladderane gives the ladderane bilayer fluidity, which we propose is achieved by increasing $\Delta S_{melting}$ by introducing an additional gain of conformational flexibility in the fluid phase. Without being bound to any particular theory, it is proposed that ladderane-ladderane packing interactions in the gel phase (which stabilize, lowering enthalpy H) are preserved in the fluid phase to such an extent that they do not greatly raise $T_m$. These interactions, retained in the fluid phase, give rise to desirable properties.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

Notwithstanding the appended claims, the disclosure set forth herein is also described by the following clauses.

Clause 1. A method of preparing a ladderane compound, the method comprising preparing a compound of formula (II) from a compound of formula (I); and a compound of formula (III) from a compound of formula (II):

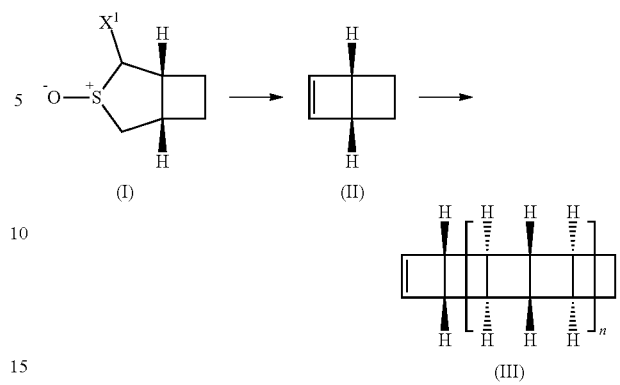

Clause 2. The method according to clause 1, wherein the method further comprises preparing a compound of formula (IV) from the compound of formula (III):

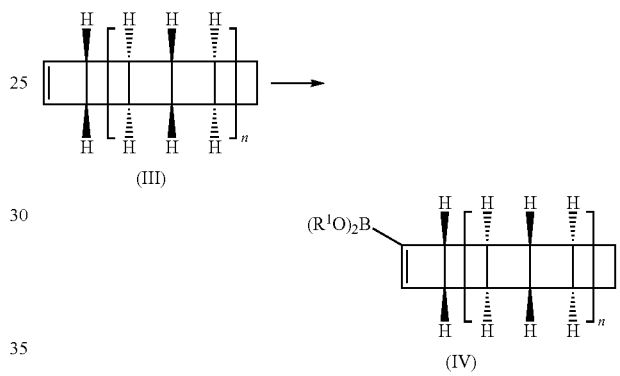

wherein n is an integer from 1 to 6; and each R' is independently an alkyl or a substituted alkyl and are optionally cyclically linked.

Clause 3. The method according to clause 2, further comprising preparing a compound of formula (V) from a compound of formula (IV):

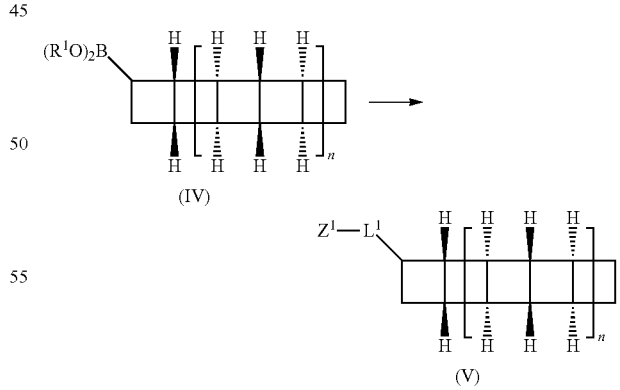

wherein:
each $R^1$ is independently an alkyl or a substituted alkyl and are optionally cyclically linked;
$L^1$ is a linker; and
$Z^1$ is a chemoselective functional group or tag; and
n is an integer from 1 to 6.

Clause 4. The method according to clause 3, wherein $L^1$ is a linker selected from an aliphatic hydrocarbon that is saturated or unsaturated, linear or branched, substituted or unsubstituted; and $Z^1$ is selected from the group consisting of, carboxylic acid, alcohol, ester, ether, amine, amide and thiol.

Clause 5. The method according to clause 1, wherein the method further comprises preparing a compound of formula (VI) from a compound of formula (IIb) and a compound of formula (VII):

[Chemical structures of (VII), (IIIb), and (VI)]

wherein:
$X^2$ is a halogen; and
m is 0 or an integer from 1 to 6.

Clause 6. The method according to clause 5, further comprising preparing a compound of formula (VIII) from a compound of formula (VI):

[Chemical structures of (VI) and (VIII)]

wherein:
$X^2$ is a halogen;
$L^1$ is a linker;
$Z^1$ is a chemoselective group or tag; and
m is 0 or an integer from 1 to 6.

Clause 7. The method according to clause 6, wherein $L^1$ is a linker selected from an aliphatic hydrocarbon that is saturated or unsaturated, linear or branched, substituted or unsubstituted; and $Z^1$ is selected from the group consisting of, carboxylic acid, alcohol, ester, ether, amine, amide and thiol.

Clause 8. The method according to clause 3, 4, 6 or 7, further comprising preparing a compound of formula (IX) from compounds selected from formulas (V) and (VIII):

$$Y^1\text{-}L^2\text{-}[\text{-}L^1\text{-}X^3]_p \qquad (IX)$$

wherein:
$X^3$ is selected from the group consisting of:

[Chemical structures]

$L^1$ is a linker selected from an aliphatic hydrocarbon that is saturated or unsaturated, linear or branched, substituted or unsubstituted; and $L^2$ is an optional linker (e.g. a glycerol, polyglycerol, amino glycerol, polyol, peptide)

n is an integer from 1 to 6;

m is 0 or an integer from 1 to 6;

p is 1 or 2; and $Y^1$ is a hydrophilic head group.

Clause 9. The method according to clause 6, wherein $Y^1$ is selected from the group consisting of a phosphate, substituted phosphate, amine, substituted amine, polyamine, polyol, hydroxyl (OH), carboxylate ($COO^-$), sulfate ($SO_4$), sulfonate ($SO_3^-$) and carbohydrate.

Clause 10. The method according to clause 9, wherein the hydrophilic head group is selected from the group consisting of phosphocholine, phosphoethanolamine, phosphoserine, phosphoinositol, ethylphosphophorylcholine, polyethyleneglycol, melamine, glucosamine, trimethylamine.

Clause 11. The method according to any one of clauses 8 to 10, wherein the compound of formula (IX) has a structure of formula (X) or (XI):

[Chemical structures of (X) and (XI)]

and the method comprises, reacting a ladderane compound of formula (V) or (VIII)

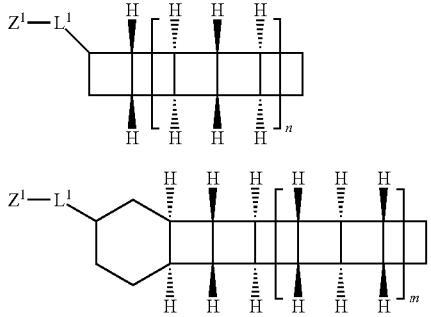

(V)

(VIII)

with a glycerol derivative of formula (XII)

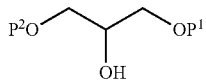

(XII)

and a phosphorylation reagent, wherein:
$X^3$ is selected from the group consisting of:

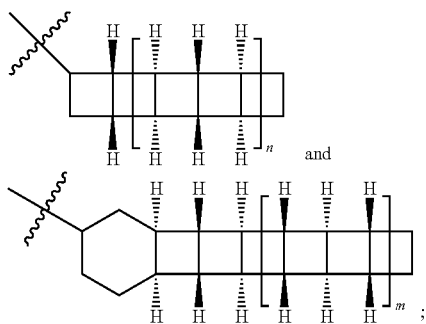

and

;

$L^1$ is a linker (e.g., an aliphatic hydrocarbon that is saturated or unsaturated, linear or branched, substituted or unsubstituted);
$Z^1$ is a chemoselective functional group (e.g., a group selected from the group consisting of, carboxylic acid, alcohol, ester, ether, amine, amide, thiol);
n is an integer from 1 to 6;
m is 0 or an integer from 1 to 6;
$P^1$ is H or a protecting group; and
$P^2$ is a protecting group.

Clause 12. The method according to clause 11, further comprising preparing a compound of formula (X) from a compound of formula (XI) via a compound of formula (XIII):

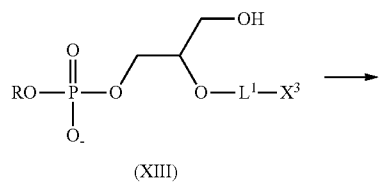

(XIII)

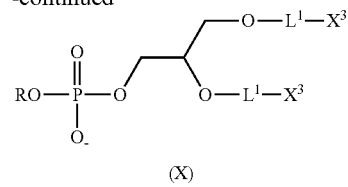

(X)

wherein each $X^3$ group are different.

Clause 13. The method according to clause 11 or 12, wherein R in formulas (X) and (XI) is:

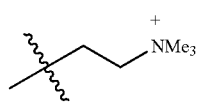

Clause 14. The method according to clause 2, wherein the compound of formula (IV) is prepared by enantioselective hydroboration, in 80% or more e.e.

Clause 15. The method according to clause 3, clause 4, and any one of clauses 6 to 13, wherein $L^1$ is a linear aliphatic hydrocarbon comprising 4-10 carbons.

Clause 16. The method according to clause 3, wherein $Z^1$ is a carboxylic acid group.

Clause 17. The method according to clause 6, wherein $Z^1$ is an alcohol.

Clause 18. The method according to clause 3, clause 4, and any one of clauses 8 to 13, wherein the compound of formula (V) is:

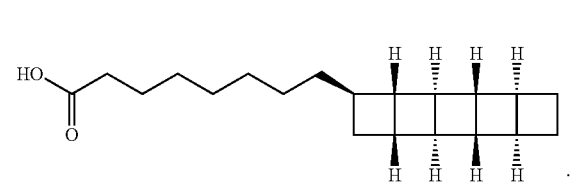 [SMILES: O=C(O)CCCCCCC[C@@H]1C[C@H]2[C@@H]3[C@H]4[C@@H]5CC[C@@H]5[C@H]4[C@@H]3[C@@H]12]

Clause 19. The method according to any one of clauses 6 to 13, wherein the compound of formula (VIII) is:

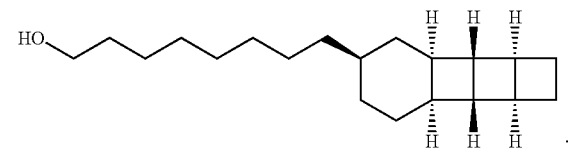 [SMILES: OCCCCCCCC[C@@H]1CC[C@H]2[C@@H](C1)[C@@H]1[C@H]3CC[C@H]3[C@H]21]

Clause 20. The method according to any one of clauses 1 to 19, which further comprises one or more purification steps.

Clause 21. A method of preparing a liposome, comprising hydrating one or more compounds of any one of clauses 8 to 13 under conditions sufficient to form a liposome.

Clause 22. The method according to clause 21, wherein the liposome forms giant unilamellar vesicles (GUVs).

Clause 23. The method according to clause 21, wherein the liposome forms small unilamellar vesicles (SUVs).

Clause 24. The method according to any one of clauses 21 to 23, further comprising loading with one or more cargo moieties during, or after liposome formation.

Clause 25. A ladderane compound or precursor thereof, having one of the following formula:

(III) [structure showing ladderane with H substituents, subscript n]

(IV) [structure showing $(R^1O)_2B$—ladderane with H substituents, subscript n]

(VI) [structure showing quinone with $X^2$ attached to ladderane, subscript m]

(VIII) [structure showing $Z^1$—$L^1$—cyclohexyl-ladderane, subscript m]

(V) [structure showing $Z^1$—$L^1$—ladderane, subscript n]

wherein:

n is an integer from 1 to 6;

m is 0 or an integer from 1 to 6;

$R^1$ is independently an alkyl or a substituted alkyl and are optionally cyclically linked (e.g., a cyclic pinacol ester);

$X^2$ is a leaving group (e.g., a halogen);

$L^1$ is a linker (e.g., a linear linker selected from an aliphatic hydrocarbon that is saturated or unsaturated, linear or branched, substituted or unsubstituted); and $Z^1$ is a chemoselective functional group (e.g., selected from the group consisting of, carboxylic acid, alcohol, ester, ether, amine, amide, thiol).

Clause 26. The ladderane compound according to clause 25, wherein $L^1$ is a linear aliphatic hydrocarbon comprising 4-10 carbons.

Clause 27. The ladderane compound according to clause 25 or 26, wherein $Z^1$ is s carboxylic acid group.

Clause 28. The ladderane compound according to clause 25 or 26, wherein $Z^1$ is an alcohol group.

Clause 29. The ladderane compound according to clause 25, wherein $X^2$ is bromide.

Clause 30. The ladderane compound according to clause 25, wherein the compound of formula (V) is:

[structure: HO-C(=O)-alkyl chain-ladderane with H substituents]

Clause 31. The ladderane compound according to clause 25, wherein the compound of formula (VIII) is:

[structure: HO-alkyl chain-cyclohexyl-ladderane with H substituents]

Clause 32. A composition comprising:
a liposome carrier comprising a ladderane lipid of formula (IX):

$$Y^1\text{-}L^2\text{-}[\text{-}L^1\text{-}X^3]_p \quad (IX)$$

wherein:

$X^3$ is selected from the group consisting of:

[structure showing ladderane with H substituents, subscript n] and

[structure showing cyclohexyl-ladderane with H substituents, subscript m];

$L^1$ is a linker (e.g., a first linear linker selected from an aliphatic hydrocarbon that is saturated or unsaturated, linear or branched, substituted or unsubstituted); and $L^2$ is an optional linker (e.g. a second linker selected from glycerol, polyglycerol, amino glycerol, polyol, peptide);

n is an integer from 1 to 6;

m is 0 or an integer from 1 to 6;

p is 1 or 2; and $Y^1$ is a hydrophilic head group; and one or more cargo moieties encapsulated in the liposome carrier.

Clause 33. The composition according to clause 32, wherein one or more cargo moieties are selected from the group consisting of an enzyme, a pharmaceutical agent, a plasmid, a polynucleotide, a polypeptide, a sensor, a metal, a polymer, a cell targeting agent, a detectable label and a combination thereof.

Clause 34. The composition according to clause 32 or 33, further comprising one or more tags on the ladderane lipid of formula (IX).

Clause 35. The composition according to clause 34, wherein the tag is a chemoselective tag or an affinity tag.

Clause 36. A method of administering a pharmaceutical agent to a subject in need thereof, the method comprising:
administering to a subject a liposomal composition according to any one of clauses 32 to 35 under conditions sufficient to deliver the liposomal composition to a site of interest in the subject, and release the pharmaceutical agent from the liposomal composition at the site of interest.

Clause 37. The method according to clause 36, wherein the site of interest is a tumor.

Clause 38. The method according to clause 36 or 37, wherein the pharmaceutical agent is a chemotherapy agent.

What is claimed is:

1. A method of preparing a ladderane compound, the method comprising:
   preparing a compound of formula (II) from a compound of formula (I); and
   preparing a ladderane compound of formula (III) from the compound of formula (II):

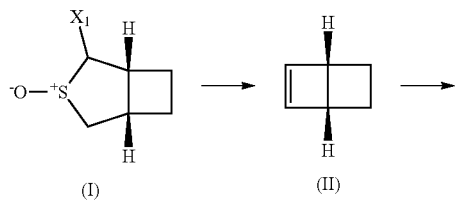

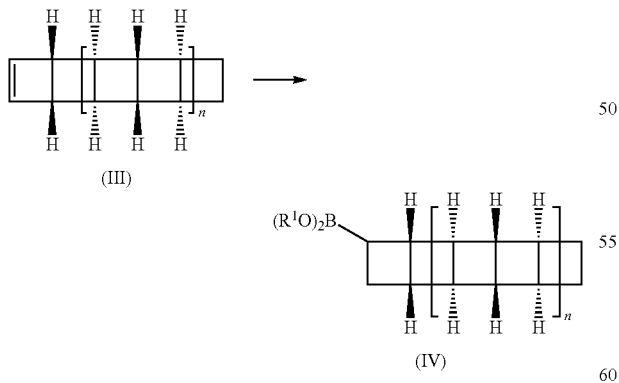

wherein $X^1$ is a leaving group, and n is an integer from 1 to 6.

2. The method according to claim 1, wherein the method further comprises preparing a compound of formula (IV) from the compound of formula (III):

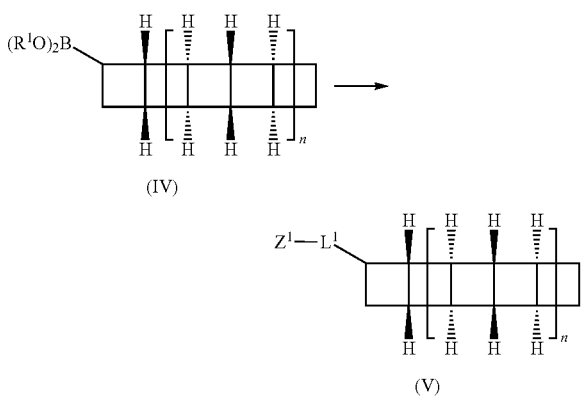

wherein n is an integer from 1 to 6; and each $R^1$ is independently an alkyl or a substituted alkyl and are optionally cyclically linked.

3. The method according to claim 2, further comprising preparing a compound of formula (V) from a compound of formula (IV):

wherein:
each $R^1$ is independently an alkyl or a substituted alkyl and are optionally cyclically linked;
$L^1$ is a linker; and
$Z^1$ is a chemoselective functional group or tag; and
n is an integer from 1 to 6.

4. The method according to claim 1, wherein the method further comprises preparing a compound of formula (VI) from a compound of formula (II) or (III), and a compound of formula (VII):

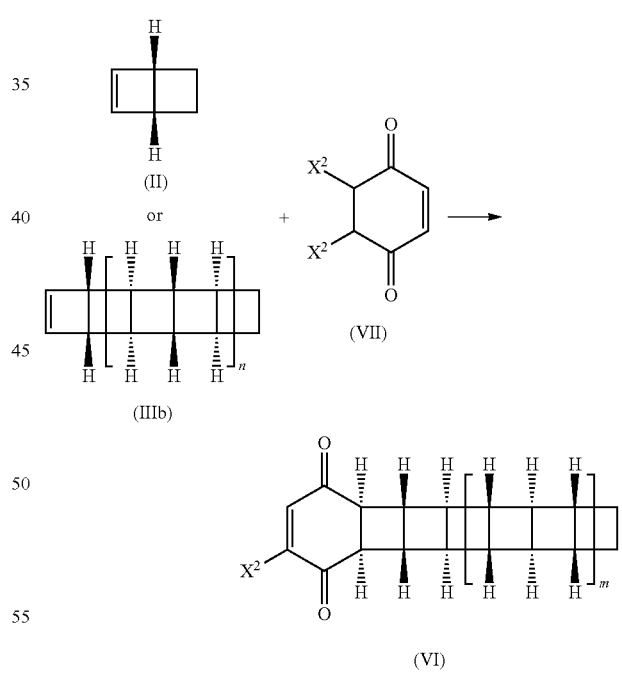

wherein:
$X^2$ is a halogen;
n is an integer from 1 to 6; and
m is 0 or an integer from 1 to 6.

5. The method according to claim 4, further comprising preparing a compound of formula (VIII) from a compound of formula (VI):

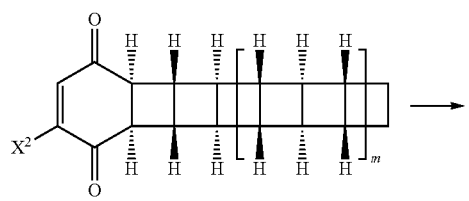

(VI)

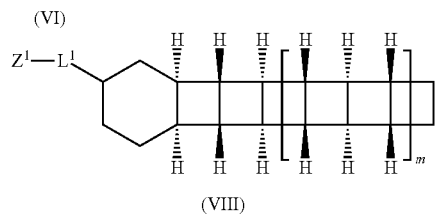

(VIII)

wherein:

X² is a halogen;

L¹ is a linker;

Z¹ is a chemoselective group or tag; and m is 0 or an integer from 1 to 6.

6. A method of preparing a ladderane compound of formula (IX) from a compound selected from one of formulae (V) and (VIII):

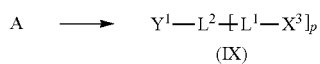

(IX)

wherein:

A is selected from a compound of formulae (V) and (VIII):

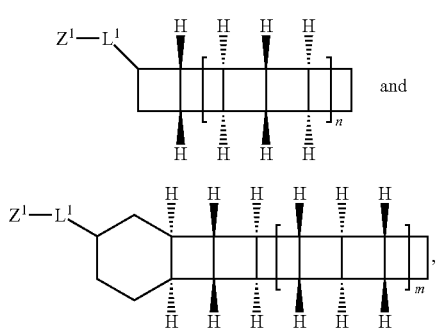

L¹ is a linker;

Z¹ is a chemoselective group or a tag;

X³ is selected from the group consisting of:

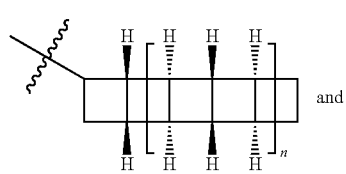

and

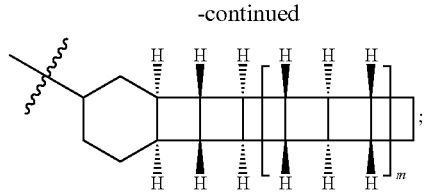

L² is an optional linker;

n is an integer from 1 to 6;

m is 0 or an integer from 1 to 6;

p is 1 or 2; and

Y¹ is a hydrophilic head group.

7. The method according to claim 6, wherein the hydrophilic head group is selected from the group consisting of phosphocholine, phosphoethanolamine, phosphoserine, phosphoinositol, ethylphosphophorylcholine, polyethyleneglycol, melamine, glucosamine, trimethylamine.

8. The method according to claim 6, wherein the compound of formula (IX) is of formula (X) or (XI):

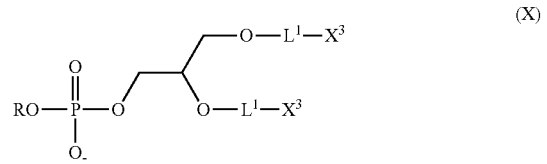

(X)

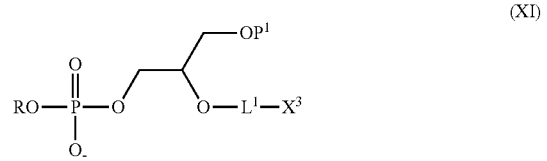

(XI)

and the method comprises, reacting a ladderane compound of formula (V) or (VIII)

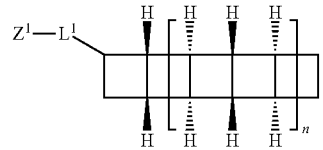

(V)

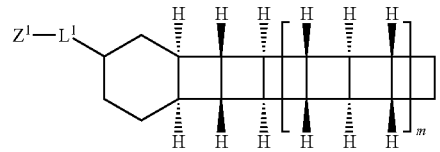

(VIII)

with a glycerol derivative of formula (XII)

(XII)

and a phosphorylation reagent, wherein:

X³ is selected from the group consisting of:

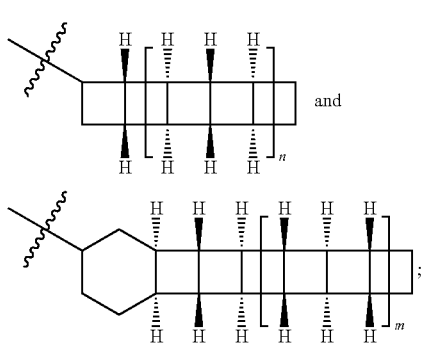

R is H, or R together with the oxygen atom to which it is attached forms a group selected from, choline, ethanolamine, serine, and inositol;

L¹ is a linker;

Z¹ is selected from the group consisting of, carboxylic acid, alcohol, ester, ether, amine, amide, and thiol;

n is an integer from 1 to 6;

m is 0 or an integer from 1 to 6;

P¹ is H or a protecting group; and

P² is a protecting group.

9. The method according to claim 8, further comprising preparing a compound of formula (X) from a compound of formula (XI) via a compound of formula (XIII):

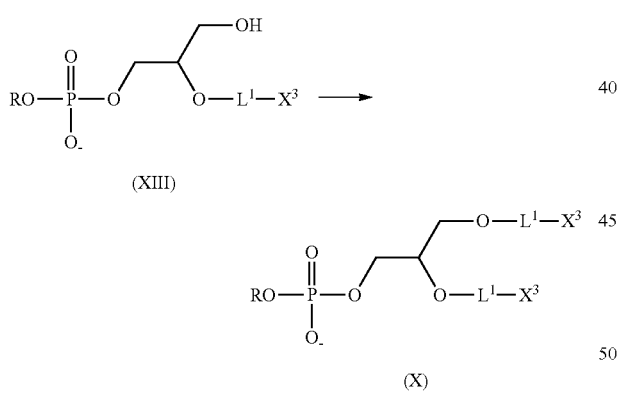

wherein each X³ group are different.

10. The method according to claim 8, wherein R in formulas (X) and (XI) is:

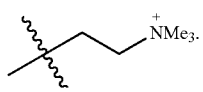

11. The method according to claim 2, wherein the compound of formula (IV) is prepared by enantioselective hydroboration, in 80% or more e.e.

12. The method according to claim 3, wherein the compound of formula (V) is:

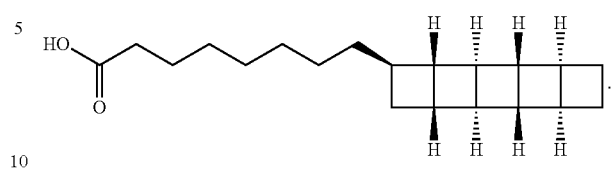

13. The method according to claim 5, wherein the compound of formula (VIII) is:

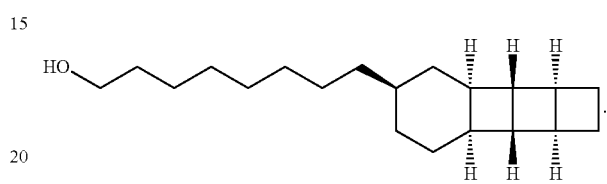

14. A ladderane compound, having one of the following formula:

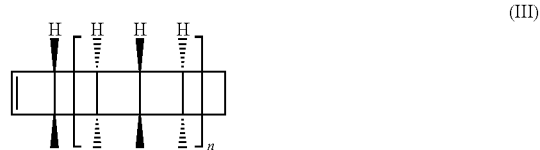

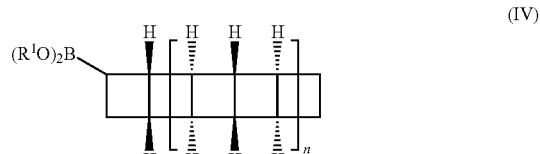

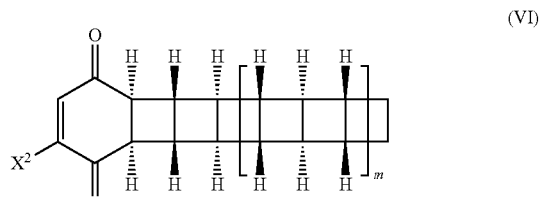

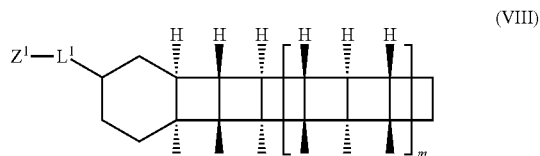

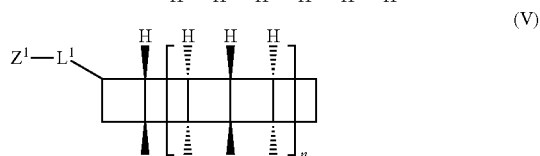

wherein:

n is an integer from 1 to 6;

m is 0 or an integer from 1 to 6;

each R¹ is independently an alkyl or a substituted alkyl and are optionally cyclically linked;

$X^2$ is a halogen;

$L^1$ is a linker; and $Z^1$ is selected from the group consisting of, ester, ether, amine, amide, and thiol.

15. The ladderane compound according to claim 14, wherein $L^1$ is an aliphatic hydrocarbon that is saturated or unsaturated, linear or branched, substituted or unsubstituted.

16. A composition comprising:

a liposome carrier comprising a ladderane lipid of formula (IX):

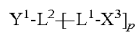 (IX)

wherein:

$X^3$ is selected from the group consisting of:

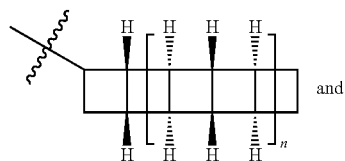 and

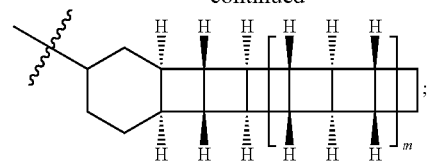;

$L^1$ is a linker; and $L^2$ is an optional linker;

n is an integer from 1 to 6;

m is 0 or an integer from 1 to 6;

p is 1 or 2; and $Y^1$ is a hydrophilic head group; and one or more cargo moieties encapsulated in the liposome carrier.

17. The composition according to claim 16, wherein the one or more cargo moieties are selected from the group consisting of an enzyme, a pharmaceutical agent, a plasmid, a polynucleotide, a polypeptide, a sensor, a metal, a polymer, a cell targeting agent, a detectable label and a combination thereof.

18. The composition according to claim 16, wherein the one or more cargo moieties are a chemotherapeutic agent.

* * * * *